US011311631B2

(12) United States Patent
Markovic et al.

(10) Patent No.: US 11,311,631 B2
(45) Date of Patent: Apr. 26, 2022

(54) PACLITAXEL-ALBUMIN-BINDING AGENT COMPOSITIONS AND METHODS FOR USING AND MAKING THE SAME

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 16/328,146

(22) PCT Filed: Sep. 6, 2017

(86) PCT No.: PCT/US2017/050355
§ 371 (c)(1),
(2) Date: Feb. 25, 2019

(87) PCT Pub. No.: WO2018/048958
PCT Pub. Date: Mar. 15, 2018

(65) Prior Publication Data
US 2019/0184032 A1    Jun. 20, 2019

Related U.S. Application Data

(60) Provisional application No. 62/384,119, filed on Sep. 6, 2016.

(51) Int. Cl.
A61K 47/69        (2017.01)
A61K 47/64        (2017.01)
(Continued)

(52) U.S. Cl.
CPC ........ *A61K 47/6929* (2017.08); *A61K 31/337* (2013.01); *A61K 47/54* (2017.08);
(Continued)

(58) Field of Classification Search
None
See application file for complete search history.

(56) References Cited

U.S. PATENT DOCUMENTS 4,350,687 A    9/1982   Lipton et al.
5,026,772 A    6/1991   Kobayashi et al.
(Continued)

FOREIGN PATENT DOCUMENTS

CN    1237901 A      12/1999
CN    102458112 A     5/2012
(Continued)

OTHER PUBLICATIONS

Chuang et al. (Recombinant human serum albumin; Drugs Today 2007, 43(8);547). (Year: 2007).*
(Continued)

*Primary Examiner* — Melissa S Mercier
(74) *Attorney, Agent, or Firm* — Baker Botts L.L.P.

(57) ABSTRACT

Described herein are nanoparticle compositions comprising binding agents, carrier proteins and an amount of paclitaxel derivative, and optionally a therapeutic agent. Also described herein are nanoparticle compositions comprising carrier proteins and an amount of paclitaxel, and optionally binding agents and/or a therapeutic agent, wherein the paclitaxel is present in an amount that is less than an amount that provides a therapeutic effect. Also disclosed herein are nanoparticles which contain (a) carrier protein, (b) a paclitaxel derivative, the paclitaxel derivative having reduced toxicity compared to paclitaxel, and optionally (c) a binding agent and/or (d) a therapeutic agent. Also described are
(Continued)

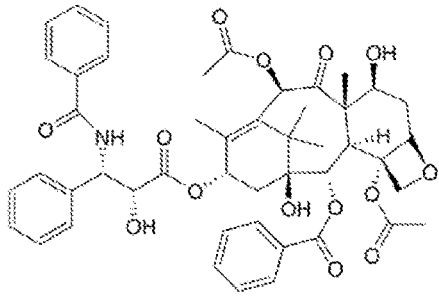

Paclitaxel $[(CH_3CH_2)_3O]BF_4$

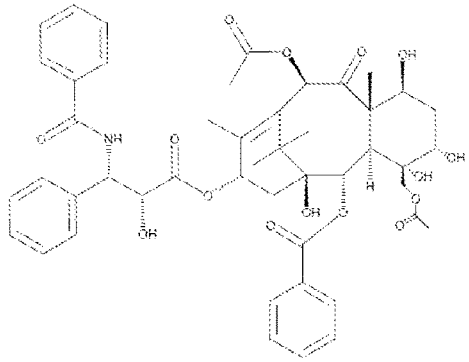

20-Acetoxy-4-deactyl-5-epi-20, O-secotaxol
(The Meerwein Product of Paclitaxel)

methods of making and using the same, in particular, as a cancer therapeutic.

17 Claims, 5 Drawing Sheets

(51) Int. Cl.
  *A61K 47/54* (2017.01)
  *A61K 47/68* (2017.01)
  *A61P 35/00* (2006.01)
  *A61K 31/337* (2006.01)

(52) U.S. Cl.
  CPC ........ *A61K 47/643* (2017.08); *A61K 47/6803* (2017.08); *A61K 47/6851* (2017.08); *A61P 35/00* (2018.01)

(56) References Cited

U.S. PATENT DOCUMENTS

| | | |
|---|---|---|
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 5,916,596 A | 6/1999 | Desai et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,533,058 B2 | 1/2017 | Markovic et al. |
| 9,555,128 B2 | 1/2017 | Markovic et al. |
| 9,566,350 B2 | 2/2017 | Markovic et al. |
| 9,757,453 B2 | 9/2017 | Markovic et al. |
| 10,279,035 B2 | 5/2019 | Markovic et al. |
| 10,279,036 B2 | 5/2019 | Markovic et al. |
| 10,300,016 B2 | 5/2019 | Markovic et al. |
| 10,307,482 B2 | 6/2019 | Markovic et al. |
| 10,322,084 B2 | 6/2019 | Markovic et al. |
| 10,376,579 B2 | 8/2019 | Markovic et al. |
| 10,376,580 B2 | 8/2019 | Markovic et al. |
| 10,391,055 B2 | 8/2019 | Markovic et al. |
| 10,406,224 B2 | 9/2019 | Markovic et al. |
| 10,413,606 B2 | 9/2019 | Markovic et al. |
| 10,420,839 B2 | 9/2019 | Markovic et al. |
| 10,441,656 B2 | 10/2019 | Markovic et al. |
| 10,471,145 B2 | 11/2019 | Markovic et al. |
| 10,478,495 B2 | 11/2019 | Markovic et al. |
| 10,493,150 B2 | 12/2019 | Markovic et al. |
| 10,507,243 B2 | 12/2019 | Markovic et al. |
| 10,561,726 B2 | 2/2020 | Swiss et al. |
| 10,596,111 B2 | 3/2020 | Markovic et al. |
| 10,596,112 B2 | 3/2020 | Markovic et al. |
| 10,610,484 B2 | 4/2020 | Markovic et al. |
| 10,618,969 B2 | 4/2020 | Markovic et al. |
| 10,624,846 B2 | 4/2020 | Markovic et al. |
| 10,668,151 B2 | 6/2020 | Markovic et al. |
| 10,765,741 B2 | 9/2020 | Markovic et al. |
| 10,772,833 B2 | 9/2020 | Markovic et al. |
| 10,780,049 B2 | 9/2020 | Markovic et al. |
| 10,780,050 B2 | 9/2020 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1* | 6/2007 | Dang .................. A61K 31/427 424/93.4 |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1* | 5/2010 | Desai .................. A61K 9/0019 424/499 |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavle et al. |
| 2013/0164816 A1 | 6/2013 | Chang et al. |
| 2013/0195983 A1 | 8/2013 | Desai et al. |
| 2014/0056909 A1 | 2/2014 | Markovic |
| 2014/0155344 A1 | 6/2014 | Desai et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1* | 9/2015 | Markovic .......... A61K 47/6803 424/499 |
| 2016/0339118 A1 | 1/2016 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic |
| 2017/0106087 A1 | 4/2017 | Markovic et al. |
| 2017/0128408 A1 | 5/2017 | Markovic |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |

(56) References Cited

U.S. PATENT DOCUMENTS

| | | |
|---|---|---|
| 2017/0182186 A1 | 6/2017 | Markovic et al. |
| 2017/0182187 A1 | 6/2017 | Markovic |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0182185 A1 | 8/2017 | Markovic et al. |
| 2017/0216453 A1 | 8/2017 | Markovic et al. |
| 2017/0232102 A1 | 8/2017 | Markomc et al. |
| 2017/0291952 A1 | 10/2017 | Markovic et al. |
| 2018/0235886 A1 | 8/2018 | Markovic et al. |
| 2019/0022188 A1 | 1/2019 | Markovic |
| 2019/0038761 A1 | 2/2019 | Markovic et al. |
| 2019/0099498 A1 | 4/2019 | Markovic et al. |
| 2019/0201546 A1 | 7/2019 | Markovic et al. |
| 2019/0202916 A1 | 7/2019 | Markovic et al. |
| 2019/0216944 A1 | 7/2019 | Markovic et al. |
| 2020/0237907 A1 | 7/2020 | Swiss et al. |
| 2020/0268884 A1 | 8/2020 | Markovic et al. |

FOREIGN PATENT DOCUMENTS

| | | |
|---|---|---|
| EP | 0505047 A1 | 9/1992 |
| EP | 1913947 | 4/2008 |
| EP | 3204413 | 8/2017 |
| EP | 3533870 | 9/2019 |
| JP | S60146833 | 8/1985 |
| JP | S6178731 | 4/1986 |
| JP | H04504253 | 7/1992 |
| JP | 5-78342 | 3/1993 |
| JP | 2001-501931 | 2/2001 |
| JP | 2001072589 | 3/2001 |
| JP | 2012522809 | 9/2012 |
| JP | 2012-523433 | 10/2012 |
| KR | 1020090078330 | 7/2009 |
| RU | 2011133819 | 2/2013 |
| RU | 2505315 C2 | 1/2014 |
| WO | 89/1 0398 | 11/1989 |
| WO | 97/49390 | 12/1997 |
| WO | 99/00113 | 1/1999 |
| WO | 99/51248 | 10/1999 |
| WO | 2004/022097 | 3/2004 |
| WO | 2004/096224 | 11/2004 |
| WO | 2006034455 | 3/2006 |
| WO | 2008/057562 | 5/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 I | 5/2008 |
| WO | 2008/112987 | 9/2008 |
| WO | 2009/043159 | 4/2009 |
| WO | 2009/055343 | 4/2009 |
| WO | 2010/003057 | 1/2010 |
| WO | 2010/014117 A1 | 2/2010 |
| WO | 2010/017216 | 2/2010 |
| WO | 2010/118365 | 10/2010 |
| WO | 2010/124009 | 10/2010 |
| WO | 2010136492 | 12/2010 |
| WO | 2012/048223 | 4/2012 |
| WO | 2012/088388 | 6/2012 |
| WO | 2012/154861 | 11/2012 |
| WO | 2014/009774 | 1/2014 |
| WO | 2014/037422 | 3/2014 |
| WO | 2014/055415 | 4/2014 |
| WO | 2014/055415 I | 4/2014 |
| WO | 2014/105644 | 7/2014 |
| WO | 2014/123612 | 8/2014 |
| WO | 2015/048520 | 4/2015 |
| WO | 2015/191969 | 12/2015 |
| WO | 2015/195476 | 12/2015 |
| WO | I 2015/191969 | 12/2015 |
| WO | 2016/057554 | 4/2016 |
| WO | 2016/059220 | 4/2016 |
| WO | 2016/089873 | 6/2016 |
| WO | 2017/031368 | 2/2017 |
| WO | 2017/062063 | 4/2017 |
| WO | 2017/120501 | 7/2017 |
| WO | 2017/139698 | 8/2017 |
| WO | 2017/165439 | 9/2017 |
| WO | 2017/165440 | 9/2017 |
| WO | 2017/176265 | 10/2017 |
| WO | 2018/027205 | 2/2018 |
| WO | 2018/045238 | 3/2018 |
| WO | 2018/045239 | 3/2018 |
| WO | 2018/048815 | 3/2018 |
| WO | 2018/048816 | 3/2018 |
| WO | 2018/048958 | 3/2018 |

OTHER PUBLICATIONS

Barua et al. (Particle shape enhances specificity of antibody-display nanoparticles, PNAS, Feb. 26, 2013 110 (9) 3270-3275. (Year: 2013).*
U.S. Appl. No. 15/225,428, office action dated Jul. 31, 2019.
U.S. Appl. No. 15/225,542; office action dated Jul. 18, 2019.
U.S. Appl. No. 15/286,024, office action dated Aug. 1, 2019.
U.S. Appl. No. 15/359,569, office action dated Jul. 26, 2019.
U.S. Appl. No. 15/456,391; office action dated Jul. 24, 2019.
U.S. Appl. No. 15/456,395; office action dated Aug. 14, 2019.
U.S. Appl. No. 15/456,399; office action dated Aug. 14, 2019.
U.S. Appl. No. 15/460,552; office action dated Aug. 14, 2019.
U.S. Appl. No. 15/460,699; office action dated Aug. 28, 2019.
U.S. Appl. No. 15/461,288; office action dated Aug. 28, 2019.
Belldegrun et al. "Human Renal Carcinoma Line Transfected with Interleukn-2 and/or Interferon alpha Gene(s): Implications for Live Cancer Vaccines", J National Cancer Institute 85(3):207-216 (1993).
Buechner "Intralesional interferon alfa-2b in the treatment of basal cell carcinoma", J Am Acad Dermatol 24:731-734 (1991).
Doveil et al. "Adjuvant Therapy of Stage lllb Melanoma with Interferon Alfa-2b:Clinical and Immunological Relevance", Dermatology 191:234-239 (1995).
European Application No. 17736453.6, Extended European Search Report dated Jul. 8, 2019.
International Preliminary Report on Patentability for Application No. PCT/US2017/050134 dated Mar. 21, 2019.
Khallouf et al. "5-Fluorouracil and Interferan-alpha Immunochemotherapy Enhances Immunogenicity of Murine Pancreatic Cancer Through Upregulation of NKG2D Ligands and MHC Class 1", Immunother 35(3):245-253 (2012).
Korthals et al. "Monocyte derived dendritic ceils generated by IFN-alpha acquire mature dendritic and natural killer cell properties as shown by gene expression analysis", J Translated Medicine 5:46 (2007) (11 pages).
"Concurrent Infusions", J Oncol Pract, 4(4) 171, Jul. 2008,.
Abraxane® for Injectable Suspension .(paclitaxel protein-bound particles for injectable suspension) (albumin-bound), [drug label], 22 pages. Sep. 2009.
Abraxis Bioscience, Inc., "Abraxane: For the adjuvant treatment of node-positive breast cancer administered sequentially to standard doxorubicin-containing combination chemotherapy," Oncologic Drugs Advisory Committee Meeting (available to public Aug. 4, 2006).
Adams et al., "(P2-11 -01) Safety and clinical activity of atezolizumab (anti-PDL1) in combination with nab-paclitaxel in patients with metastatic triple-negative-breast cancer", 2 015, XP002775314, 2015 San Antonio Breast Cancer Symposium, URL: http://sabcs.org/portals/sabcs2016/documents/sabcs-2015-abstracls.pdf?v-5.
Adams et al., "Phase lb trial of atezolizumab in .combination with nab-paclitaxel in patients with metastatic triplenegative breast cancer (mTNBC)" Journal of Clinical Oncology col. 34, No. 15, May 1, 2016, 4 pages,.
Agarwal et al., "Flow Cytometric analysis of Thl and Th2 cytokines .in PBMCs as a parameter of immunological dysfunction in patients of Superficial Transitional ceil carcinoma of bladder". Cancer Immunol Immunother., 2006, 55 K6):734-743.
Agarwala et al., "Randomized phase 111 study of paclitaxel plus carboplatin with or without sorafenib as-second-line treatment in patients with advanced melanoma", J. Clin. Oncol, 2007, 25(185)8510 (Abstract).

(56) References Cited

OTHER PUBLICATIONS

Allen "Ligand-targeted therapeutics in anticancer therapy.. Cancer"; Oct. 2002,2(10), pp. 750-763.
Alley et al., "Contribution of Linker Stability to the Activities of Anilcancer Immunoconjugates", Bioconjugate Chern., 2008, 19(3). pp. 759-765.
Anonymous, "A Phase U, muiticenter, randomized, double-blind placeho-controlled trial evaluating the efficacy and safety of bevacizumab in combination with carboplatin and paclitaxel chemotherapy for the first-line treatment of patients with metastatic melanoma", U.S. National Institutes of Health, 2007,. 3 pages,.
Anonymous, "A Phase III, Multicenter, Randomized Placebo-Controlled Study of Atezolizamab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015.1 page.
Anonymous. "AtezolizumabPlus Abraxane Promising New Treatment for Triple-Negative Breast Cancer", UNM Comprehensive Cancer Center, January7, 2016, pp. 1-2.
Anonymous, "Phase II trial of carboplatin, weekly paclitaxel and biweekly bevacizumab in patients with unresectable stage IV melanoma", U.S, National Institutes of Health, 2007, 4 pages.
Anonymous "A Study of Bevacizumab With Carboplatin and Paclitaxel Chemotherapy for the First-Line Treatment of Patients With Metastatic Melanoma (BEAM)," ClinicalTrials.gav [online], Retrieved from the Internet: URL: https://clinicaltriais.gov/archive/NCT0Q434252/200703 12, dated Mar. 12, 2007, 3 pages.
U.S. Appl. No. 14/116,619, office action dated Feb. 4, 2015.
U.S. Appl. No. 14/116,619, office action dated Apr. 28, 2016.
U.S. Appl. No. 14/116,619, office action dated Sep. 10, 2015.
U.S. Appl. No. 14/432,979, office action dated Jan. 7, 2019.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Dec. 15, 2016.
U.S. Appl. No. 14/882,327, office action dated May 2, 2016.
U.S. Appl. No. 15/030,567, office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/030,568, office action dated Dec. 1, 2017.
U.S. Appl. No. 15/052,336, office action dated Jan. 22, 2019.
U.S. Appl. No. 15/052,336, office action dated Feb. 9, 2018.
U.S. Appl. No. 15/052,336, office action dated Sep. 4, 2018.
U.S. Appl. No. 15/052,623, office action dated Jan. 7, 2019.
U.S. Appl. No. 15/052,623, office action dated Feb. 9, 2018.
U.S. Appl. No. 15/052,623, office action dated May 19, 2017.
U.S. Appl. No. 15/052,623, office action dated Jul. 9, 2018.
U.S. Appl. No. 15/052,623, office action dated Nov. 25, 2016.
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433, office action dated Mar. 21, 2018.
U.S. Appl. No. 15/092,433, office action dated Aug. 10, 2018.
U.S. Appl. No. 15/092,433, office action dated Oct. 11, 2017.
U.S. Appl. No. 15/092,433; office action dated Dec. 12, 2018.
U.S. Appl. No. 15/187,672, office action dated May 31, 2018.
U.S. Appl. No. 15/167,672, office action dated Nov. 28, 2018.
U.S. Appl. No. 15/202,115, office action dated Jan. 20, 2017.
U.S. Appl. No. 15/202,115, office action dated Sep. 26, 2016.
U.S. Appl. No. 15/225,428, office action dated Aug. 14, 2018.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/225,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/331,754; office action dated Feb. 22, 2019.
U.S. Appl. No. 15/331,754; office action dated Oct. 11, 2018.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2018.
U.S. Appl. No. 15/412,536; office action dated Oct. 1, 2018.
U.S. Appl. No. 15/412,554, office action dated Sep. 27, 2018.
U.S. Appl. No. 15/412,564, office action dated Jul. 10, 2018.
U.S. Appl. No. 15/412,581; office action dated Nov. 13, 2018.
U.S. Appl. No. 15/412,596, office action dated Sep. 4, 2018.
U.S. Appl. No. 15/412,596, office action dated Dec. 27, 2018.
U.S. Appl. No. 15/412,610, office action dated Jul. 9, 2018.
U.S. Appl. No. 15/413,257; office action dated Sep. 25, 2018.
U.S. Appl. No. 15/414,526, office action dated Nov. 16, 2018.
U.S. Appl. No. 15/414,533, office action dated Nov. 19, 2018.
U.S. Appl. No. 15/414,536, office action dated Oct. 11, 2018.
U.S. Appl. No. 15/452,669, office action dated May 5, 2017.
U.S. Appl. No. 15/452,669, office action dated Nov. 16, 2017.
U.S. Appl. No. 16/452,669, office action dated Nov. 26, 2018.
Arakawa et al., "Protein-Solvent Interactions in Pharmaceutical Formulations", Pharm. Res., Mar. 1991. vol. 8, Issue 3, pp. 285-291.
Armitage et al., "New approach to classifying non-Hodgkin's lymphomas: clinical features of the major histologic subtypes. Non-Hodgkin's Lymphoma Classification Project" J Clin Oncol 16, 2780-2795 (1998).
Asadullah et al., "Interleukin-10 therapy—review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:Sll-14.
Atkins, "Interleukin-2: clinical applications", Semin Oncol., 2002, 29(3 Suppl 7):12-27.
Avastin® Bevacizumab, Roche, [drug label], 24 pages, Sep. 2008.
Baba, Oleo Science 10(1): 15-18 (Jan. 2010).
Bairagi et al., Albumin; A Versatile Drug Carrier, Austin Therapeutics. (Nov. 17, 2015) vol. 2, No. 2, p. 1021 (pp. 1-6).
Balch et al., "The new melanoma staging system", Semin Cutan Med Surg., 2003, 22(1):42-54.
Balch et al., "Update on the melanoma staging system; The importance of sentinel node staging and primary tumor mitotic rate", Journal of Surgical Oncology, Aug. 19, 2011, vol. 104, Issue-4, pp. 379-385.
Bauer et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Nab-paclitaxel and bevacizumab as first-line therapy in patients with unresectable stage III and IV melanoma", J Clinical Oncology, 2009, 27, No. 15S, abstract #9071.
Boasberg et al., "Phase II trial of nab-paclitaxel and bevacizumab as first-line therapy in patients with unresectable melanoma", Journal of Clinical Oncology, May 20, 2011, vol. 29, No. 15 Supp, 8543.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumab", Clin Transl Oncol, 2007, 9:119-120.
Carson et al., "A phase 2 trial of a recombinant humanized monoclonal anti-vascular endothelial growth factor (VEGF) antibody in patients with malignant melanoma", Proceedings of the ASCO vol.

(56) References Cited

OTHER PUBLICATIONS

22, No. 2873, General Poster Session, Thirty-Ninth Annual Meeting of the American Society of Olinical Oncology, May 31-Jun. 3, 2003. Chicago, IL, 2 pages.

Celis, "Overlapping human leukocyte antigen class I/II binding peptide vaccine fertile treatment of patients with stage IV melanoma: evidence of systemic immune dysfunction", Cancer, 2007, 110(1):203-214.

Chapman et al., "Improved Survival with Vemurafenib in Melanoma with BRAF V600E Mutation", The New England Journal of Medicine, Jun. 30, 2011, vol. 364, Issue 26, pp. 2507-2516.

Chisholm et al., "Response to influenza immunization during treatment for cancer", Arch Dis Child, 2001, 84 (6):496-500.

Chong et al., "Combining cancer vaccines with chemotherapy", Expert Opin Pharmacother., 2006, 6(16):2813-2820.

Cleland et al., "The Development of Stable Protein Formulations: A close look at protein aggregation, deamidation, and oxidation", Therapeutic Drug Carrier Systems, 1993, 10(4), pp. 307-377.

Colman, "Effects of amino acid sequence changes on antibody-antigen interactions," Research in Immunology (145 (1):33-36, (1994).

Davis, "Affinity separation of antibody-toxin conjugate from albumin-stabilized formulation", Am Biotechnol Lab., 12 (4):60-64, Mar. 1994.

DeGrasse, "A Single-Stranded DNA Aptamer That Selectively Binds to *Staphylococcus aureus* Enteroxin B", PLoS One, 2012, 7(3) e33410, pp. 1-7.

Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.

Demirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.

Denardo et al., "Inflammation and breast cancer. Balancing Immune response: crosstalk between adaptive and innate immune cells during breast cancer progression", Breast Cancer Res., 2007, 9(4):212.

Desai et al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.

Deweers et al., "Daratumumab, a novel therapeutic human CD38 monoclonal antibody, induces killing of multiple myeloma and other hematological tumors", J. Immunol., 186(3): 1840-1848, Feb. 1, 2011.

Dudek et al., "Autologous large multivalent immunogen vaccine in patients with metastatic melanoma and renal cells carcinoma", Am. J. Clin. Oncol., Apr. 1, 2008, 31(2):173-181.

Edison, "MorphoSys," 16 pages (Aug. 8, 2013).

Elbayoumi et al., "Tumor-Targeted Nanomedicines: Enhanced Antitumor Efficacy In vivo of Doxorubicin-Loaded, Long-Cirulating Liposomes Modified with Cancer-Specific Monoclonal Antibody", Clin Cancer Res., 2009, 15 (6):1973-1980.

Ellyard et al., "Th2-mediated anti-tumor Immunity: friend or foe?", Tissue Antigens, 2007, 70(1):1-11.

Elsadek et al., "Impact of albumin on drug delivery—New applications on the horizon", J of Controlled Release, 2011, 1-25.

Elst et al. "Epidermal Growth Factor Receptor Expression and Activity In Acute Myeloid Leukemia", Blood 116:3144 (2010), abstract.

Emens et al.: "(OT1-01-06) A phase III randomized trial of atezolizumab in combination with nab-paclitaxel as first line therapy for patients with metastatic triple-negative breast cancer (mTNBC)", 2015, XP002775313, 2015 San Antonio Breast Cancer Symposium, URL: http://sabcs.org/portals/sabcs2016/documents/sabcs-2015-abstracts.pdf?v=5.

European Application No. 08743903.0, Extended European Search Report datead Jan. 24, 2011.

European Application No. 09774506.1, Extended European Search Report dated Mar. 22, 2012.

European Application No. 12781802.9, Extended European Search Report dated Dec. 18, 2014.

European Application No. 13843209.1, Extended European Search Report dated Sep. 5, 2016.

European Application No. 15806443.6, Extended European Search Report dated Dec. 11, 2017.

European Application No. 15809075.3, Extended European Search Report dated Dec. 21, 2017.

Fabi et al, "Prospective study on nanoparticle albumin-bound paclitaael in advanced breast cancer: clinical results and biological observations in taxane-pretreated patients", Drug Design, Development and Therapy vol. 9, Nov. 1, 2015, 7 pages.

Ferrara et al., "The biology of VEGF and its receptors", Nat. Med., 2003, 9:669-676.

Flaherty et al., "Final Results of E2603: a double-blind, randomized phase III trial comparing carboplatin (C)/paclitaxel(P) with or without sorafenib(S) in metastatic melanoma", J. Clin Oncol., 2010, 28:15s (suppl: abstr 8511).

Folkman, "Angiogenesis in cancer, vascular, rheumatoid and other disease", Nat. Med., 1995, 1, 27-31.

Fricke et al., "Vascular endothelial growth factor-trap overcomes defects in dendritic cell differentiation but does not improve antigen-specific immune responses", Clin. Cancer Res., 2007, 13:4840-4848.

Gabrilovich et al., "Production of vascular endothelial growth factor by human tumors inhibits the functional maturation of dendritic cells", Nat. Med., 1996, 2: 1096-1103.

Gao et al., "In vivo cancer targeting and imaging with semiconductor quantum dots", Nat Biotech, 2004, 22 (8):969-976.

Gogas et al., "Chemotherapy for metastatic melanoma: time for a change?", Cancer, 2007, 109(3):455-464.

Golay et al., "Mechanism of action of therapeutic monoclonal antibodies: promises and pitfalls of in vitro and in vivo assay," Arch. Biochem. Biophys. 526(2):146-153 (2012).

Graells et al., Overproduction of VEGF165 concomitantly expressed with its receptors promotes growth and survival of melanoma cells through MAPK and P13K signaling, J. Invest. Dermatol., 2004, 123:1151-1161.

Gupta et al., "Ofatumumab, the first human anti-CD20 monoclonal antibody for the treatment of B cell hematologic malignancies," Ann. N.Y. Acad. Sci., 1263, pp. 43-56 (Jul. 25, 2012).

Haley et al., "Nanoparticles of drug delivery in cancer treatment", Urol. Oncol.: Seminars and Original Invest., 2008, 26:57-64.

Hamilton et al, "Nab-Paclitaxel/Bevacizumab/Carboplatin Chemotherapy in First-Line Triple Negative Metastatic Breast Cancer", Clinical Breast Cancer, vol. 13, No. 6, Dec. 1, 2013, 6 pages.

Hara, "What is anti-HER2 antibody tubuulin polymerization inhibitor complex T-DM1?," Pharm. Monthly 56(5);734-739 (May 2014).

Harlow et al., Antibodies: A Laboratory Manual, Cold Spring Harbor Laboratory, New York, 1988 (9 pages).

Hauschild et al., "Indivdiaulized therapy of disseminated cancer using malignant melanoma as a model", Cancer and Metastasis Reviews, 2006, 25(2): 253-256.

Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.

Hegde et al. "Predictive Impact of Circulating Vascular Endothelial Growth Factor in Four Phase III Trials Evaluating Bevacizumab," Clinical Cancer Research, Feb. 15, 2013 (Feb. 15, 2013) vol. 19, pp. 929-937.

Hersh et al., "A Phase 2 Clinical Trial of nab-Paclitaxel in Previously Treated and Chemotherapy-Naïve Patients With Metastatic Melanoma", Cancer, Jan. 1, 2010, 116:155, pp. 155-163.

Hersh et al., "A randomized, controlled phase III trial of nab-Paclitaxel versus dacarbazine in chemotherapy-naïve patients with metastatic melanoma", Ann Oncol, 2015, epub Sep. 26, 2015.

Hersh et al., "Open-label, multicenter, phase II trial of ABI-007 in previously treated and previously untreated patients with metastatic malignant melanoma", J. Clin. Oncol., 2005, 23(16S):7558 (Abstract).

(56) References Cited

OTHER PUBLICATIONS

Hobbs et al., "Regulation of Transport pathways in tumor vessels: role of tumor type and microenvironment", Proc Natl Acad Sci USA, Apr. 1998, 95, pp. 4607-4612.
Hodi et al., "Improved survival with lpilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Hood et al., Immunology, 1984, Benjamin, N.Y., 2nd edition.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323, pp. 15-16.
Huston et al., "Protein engineering of antibody binding sites: Recovery of specific activity in an anti-digoxin single-chain Fv analogue produced in *Escherichia coli*", Proc. Natl. Acad. Sci. USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
Inman, "Atezolizumab/Nab-Paclitaxel Combo Shows High Response Rates in TNBC", OneLive, Dec. 10, 2015, 4 pages.
International Preliminary Report on Patentability for Application No. PCT/US2008/057025, dated Sep. 15, 2009.
International Preliminary Report on Patentability for Application No. PCT/US2009/049511, dated Jan. 5, 2011.
International Preliminary Report on Patentability for Application No. PCT/US2012/037137, dated Nov. 12, 2013.
International Preliminary Report on Patentability for Application No. PCT/US2013/062638, dated Apr. 16, 2015.
International Preliminary Report on Patentability for Application No. PCT/US2015/035505, dated Dec. 22, 2016.
International Preliminary Report on Patentability for Application No. PCT/US2015/035515, dated Dec. 29, 2016.
International Preliminary Report on Patentability for Application No. PCT/US2015/054295, dated Oct. 13, 2016.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2017/023442, dated Oct. 4, 2018.
International Preliminary Report on Patentability for Application No. PCT/US2017/023443, dated Oct. 4, 2018.
International Preliminary Report on Patentability for Application PCT/US2016/026267, dated Apr. 10, 2018.
International Preliminary Report on Patentability for Application PCT/US2017/017553, dated Aug. 23, 2018.
International Search Report and Written Opinion for Application No. PCT/US2008/057026, dated Jul. 1, 2008.
International Search Report and Written Opinion for Application No. PCT/US2009/049511, dated Feb. 2, 2010.
International Search Report and Written Opinion for Application No. PCT/US2012/037137, dated Sep. 28, 2012.
International Search Report and Written Opinion for Application No. PCT/US2013/062638, dated Jan. 23, 2014.
International Search Report and Written Opinion for Application No. PCT/US2015/035505, dated Nov. 24, 2015.
International Search Report and Written Opinion for Application No. PCT/US2015/035515, dated Sep. 21, 2015.
International Search Report and Written Opinion for Application No. PCT/US2015/054295, dated Jan. 25, 2016.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2016/047641, dated Oct. 31, 2016.
International Search Report and Written Opinion for Application No. PCT/US2017/012580, dated Mar. 17, 2017.
International Search Report and Written Opinion for Application No. PCT/US2017/017553, dated Feb. 10, 2017.
International Search Report and Written Opinion for Application No. PCT/US2017/045643, dated Oct. 25, 2017.
International Search Report and Written Opinion for Application No. PCT/US2017/049745, dated Dec. 15, 2017.
International Search Report and Written Opinion for Application No. PCT/US2017/049746, dated Nov. 27, 2017.
International Search Report and Written Opinion for Application No. PCT/US2017/050134, dated Nov. 16, 2017.
International Search Report and Written Opinion for Application No. PCT/US2017/050137, dated Nov. 27, 2017.
Jaime et al., "Paclitaxel antibody conjugates and trehalose for preserving the immunological activity after freeze-drying," Curr Med Chem, 2004, 11(4):439-46 Abstract Only.
Jain et al., "Delivering nanomedicines to solid tumors", Nature Reviews Clinical Oncology, Nov. 2010, 7, pp. 653-664.
Jain et al., "Normalizing tumor vasculature with anti-angiogenic therapy: a new paradigm for combination therapy," Nat. Med. 7(9):987-989 (2001).
Jain, "Normalization of tumor vasculature: an emerging concept in antiangiogenic therapy," Science 307(5706):58-62 (2005).
Jazirehi et al., "Rituximab (anti-CD20) selectively modifies Bcl-xl and apoptosis protease activating factor-1 (Apaf-1) expressioni and sensitizes human non-Hodgkin's lymphoma B cell lines to paclitaxel-induced apoptosis," Mol. Cancer Ther. 2(11):1183-93 (2003).
Jiang et al., "Regulation of Immune Responses by T Cells", N Engl J Med., 2006, 354(11): 1166-1176.
Jin et al., "Paclitaxel-loaded nanoparticles decorated with anti-CD133 antibody: a targeted therapy for liver cancer stem cells," J. Nanopart. Res. 2014, 16:2157 (2014).
Julien et al, "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF121 promotes lymphangiogenesis in the sentinel lymph nodes of non-small cell lung carcinoma patients", Lung Cancer, 2008, 59(1):41-47.
Kelly et al. "Shape-Specific, Monodisperse Nano-Molding of Protein Particles," J. Am. Chem. Soc. 130:5438-5439 (2008).
Kikuchi et al., "Vascular endothelial growth factor and dendritic cells in human squamous cell carcinoma of the oral cavity", Anticancer Res., 2006. 26(3A):1833-1848.
Kim et al., "A dual target-directed agent against interleukin-6 receptor and tumor necrosis factor a ameliorates experimental arthritis", Scientific Rep. 6:20150 (2016).
Kim et al., "BEAM: A Randomized Phase II Study Evaluating the Activity of Bevacizumab in Combination with Carboplatin Plus Paclitaxel in Patients With Previously Untreated Advanced Melanoma", Journal of Clinical Oncology: official journal of the American Society of Clinical Oncology, Jan. 1, 2012, vol. 30, No. 1, pp. 34-41.
Kirkwood et al., "A pooled analysis of eastern cooperative oncology group and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chem., 5(6):602-611, Nov.-Dec. 1994.
Korman et al., "Tumor immunotherapy: preclinical and clinical activity of anti-CTLA4 antibodies", Curr Opin Invest Drugs, 2005, 6(6):582-591.

(56) References Cited

OTHER PUBLICATIONS

Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.

Kottschade et al., "A Randomized Phase 2 Study of Temozolomide and Bevacizumab or nab-Paclitaxel, Carboplatin, and Bevacizumab in Patients with Unresectable Stage IV Melanoma", Cancer, 2013, vol. 119, Issue 3, pp. 586-592.

Kratz et al., "Serum proteins as drug carriers of anticancer agents: a review", Drug Deliv., 5(4):281-299, 1998.

Kratz, "Albumin as a drug carrier: design of prodrugs, drug conjugates and nanoparticles", J Control Release, 132 (3):171-183, Epub May 17, 2008.

Krishnan et al., "Programmed death-1 receptor and interleukin-10 in liver transplant recipients at high risk for late cytomegalovirus disease", Transpl Infect Dis., 12(4):363-70, print Aug. 2010, ePub Jan. 2010.

Kukowska-Latallo et al., "Nanoparticle Targeting of Anticancer Drug Improves Therapeutic Response in Animal Model of Human Epithelial Cancer", Cancer Res, 2005, 65(12):5317-5324.

Kumar et al., Th1/Th2 cytokine imbalance in meningioma, analplastic astrocytoma and glioblastoma multiforme patients, Oncol. Ren., 2006, 15(6):1513-1516.

Lanzavecchia et al., "The use of hybrid of hybridomas to target human cytotoxic T lymphocytes", Eur. J. Immunol., 1987, 17, pp. 105-111.

Lau et al., "Is inhibition of cancer angiogenesis and growth by paclitaxel schedule dependent?", Anti- Cancer Drugs, 2004, 15:871-875.

Lee et al., "The co-delivery of paclitaxel and Herceptin using cationic micellar nanoparticles", Biomaterials vol. 30, No. 5, Feb. 1, 2009, pp. 919-927.

Lei et al., "Comparing cellular uptake and cytotoxicity of targeted drug carriers in cancer cell lines with different drug resistance mechanisms", Nanomed: Nanotech, Biol, and Med., 2011, 7:324-332.

Lev et al., "Decarbazine causes transcriptional up-regulation of interleukin 8 and vascular endothelial growth factor in melanoma cells: a possible escape mechanism from chemotherapy", Mol Cancer Ther., 2003, 2:753-763.

Lev et al., "Exposure of melanoma cells to dacarbazine results in enhanced tumor growth and metastasis in vivo", J. Clin. Oncol., 2004, 22:2092-2100.

Liang et al., "IFN-alpha regulates NK cell cytotoxicity through STAT1 pathway," Cytokine, Aug. 13, 2003 (Aug. 13, 2013), vol. 23, pp. 190-199.

Lin, "Salmon Calcitonin: Conformational Changes and Stabilizer Effects", AIMS Biophysics, 2015, 2(4):695-723.

Lloyd et al. "Modelling the human immune response: performance of a 1011 human antibody repertoire against a broad panel of therapeutically relevant antigens", Protein Eng. , Design & Selection 22(3):159-168 (2009).

Lundin et al., "Phase 2 study of alemtuzumab (anti-CD52 monoclonal antibody) in patients with advanced mycosis fungoides/Sezary syndrome", Blood (2003) vol. 101, No. 11, pp. 4267-4272.

Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.

Marcoval et al., "Angiogenesis and malignant melanoma. Angiogenesis is related to the development of vertical (tumorigenic) growth phase", J. Cutan. Pathol., 1997, 24:212-218.

Markovic et al., "A phase II study of ABT-510 (thrombospondin-1 analog) for the treatment of metastic melanoma", Am. J. Clin. Oncol., 2007, 30(3):303-309.

Markovic et al., "A reproducible method for the enumeration of functional ( cytokine producing) versus non-functional peptide-specific cytotoxic T lymphocytes in human peripheral blood", Clin. Exo. Immunol., 2006, 145:438-447.

Markovic et al., "Peptide vaccination of patients with metastatic melanoma: improved clinical outcome in patients demonstrating effective immunization", Am J Clin Oncol., 2006, 29(4):352-360.

Matejtschuk, "Lyophilization of Proteins", Methods in Molecular Biology, Cryopreservation and Freeze-Drying Protocols, Second Edition, Edited by: J.G. Day and G.N. Stacey, Humana Press Inc., Totowa, NJ, 2007, vol. 368, pp. 59-72.

Matsuda et al., Preoperative oral immunie-enhancing nutritional supplementation corrects TH1/TH2 imbalance in patients undergoing efective surgery for colorectal cancer, Dis. Colon Rectum, 2006, 49(4):507-516.

Mayo Clinic, "Paclitaxel Albumin-Stabilized Nanoparticle Formulation and Bevacizumab in Treating Patients With Stage IV Melanoma That Cannot Be Removed by Surgery", Dec. 19, 2013, ClinicalTrials.gov., URL: https://www.clinicaltrials.gov/ct2/show/NCT02020707 (Four (4) pages).

McElroy et al., "Imaging of Primary and Metastic Pancreatic Cancer Using a Fluorophore-Coniugated Anti-CA19-9 Antibody for Surgical Navigation", World j Surg., 2008, 32: 1057-1066.

Meadows et al., "Anti-VEGF Therapies in the Clinic," Cold Spring Harbor Perspectives in Medicine, Oct. 1, 2012 (Oct. 1, 2012), vol. 2, pp. 1-27.

Melcher, "Recommendations for the Influenz and pneumococcal vaccinations in people receiving chemotherapy", Clin Oncol (R Coll Radion), 2005, 17(1):12-15.

Merchan et al., "Increased endothelial uptake of paclitaxel as a potential mechanism for its antiangiogenic effects: potentiation by Cox-2 inhibition", Int. J. Cancer, 2005, 113, pp. 490-498.

Mezzaroba et al., "New potentials therapeutic approach for the treatment of B-Cell malignancies using chlorambucil/Hydroxychloroquine-Loaded Anti-CD20 Nanoparticles", Sep. 2103, PLoS ONE vol. No. 8, Issue 9 pp. 1-10, e74216.

Middleton et al., "Randomized phase III study of temozolomide versus dacarbazine in the treatment of patients with advanced metastatic malignant melanoma", J. Clin. Oncol., 2000, 18, pp. 158-166.

Miller et al., "Paclitaxel plus Bevacizumab versus Paclitaxel Alone for Metastatic Breast Cancer," N Engl. J Med., (2007) vol. 357:2666-2676.

Mimura et al., Vascular endothelial growth factor inhibits the function of human mature dendritic cells mediated by VEGF receptor-2, Cancer Immunol Immunother., 2007, 56(6). pp. 761-770.

Mirtsching et al., "A Phase II Study of Weekly Nanoparticle Albumin-Bound Paaclitaxel With or Without Trastuzumab in Metastatic Breast Cancer", Clinical Breast Cancer, 2011, 11(2):121-128.

Mocellin et al., "Cytokines and immune response in the tumor microenvironment", J Immunother., 2001, 24(5), pp. 392-407.

Motl, "Bevacizumab in combination chemotherapy for colorectal and other cancers", Am. J. Health-Svst. Pharm 2005, 62, pp. 1021-1032.

Mustacchi et al, "The role of taxanes in triple-negative breast cancer: literature review", Drug Design, Development and Therapy, vol. 9, Aug. 5, 2015, 16 pages.

Nahleh et al, "Swog S0800 (NCI CDR0000636131): addition of bevacizumba to neoadjuvant nab-paclitaxel with dose-dense doxorubicin and cyclophosphamide improves pathologic complete response (pCR) rates in inflammatory or locally advanced breast cancer", Breast Cancer Research and Treatment, vol. 158, No. 3 Jul. 8, 2016, 12 pages.

Nevala et al, "Abstract B77: Targeted nao-immune conjugates to melanoma: Preclinical testing of bevacizumab targeted nab-paclitaxel", Cancer Immunology Research, vol. 3, Oct. 1, 2015, 3 pages.

Nevala et al, "Antibody-targeted paclitaxel loaded nanoparticles for the treatment of CD20 B-cell lymphoma", Scientific Reports, vol. 7, Apr. 5, 2017, 9 pages.

Nevala et al. "Antibody-Targeted Chemotherapy for the Treatment of Melanoma", Cancer Research, vol. 76, No. 13, Jul. 1, 2016, pp. 3954-3964.

Nevala et al, "Targeted nano-immune conjugates to melanoma: Preclinical testing of bevacizumab targeted nab-paclitaxel", Pro-

(56) References Cited

OTHER PUBLICATIONS ceedings of the AACR Special Conference: Tumor Immunology and Immunotherapy: A new Chapter, Dec. 1, 2014, 2 pages.
Ng et al., "Influence of formulation vehicle on metronomic taxane chemotherapy: albumin-bound versus cremophor EL-based paclitaxel", Clin. Cancer Res., 2006, 12, pp. 4331-4338.
Ng et al., "Taxane-mediated antiangiogenesis in vitro: influence of formulation vehicles and binding proteins", Cancer Res., 2004, 64, pp. 821-824.
Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.
Nishida et al, English Translation of "Clinical Trials of New Drugs Cytotoxic Effect against Multiple Myeloma with High Expression of a CD38 Antigen and a Human CD38 Monoclonal Antibody Daratumumab:CD38 Antigen", history of Medicine, Sep. 29, 2012, vol. 242, No. 13, pp. 1176-1181.
Oku et al., "Tumor growth modulation by sense and antisense vascular endothelial growth factor gene expression: effects on angiogenesis, vascular permeability, blood volume, blood flow, fluorodeoxyglucose uptake, and proliferationi of human melanoma intracerebral xenografts", Cancer Res., 1998, 58, pp. 4185-4192.
Ortaldo et al., "Effects of several species of human leukocyte interferon on cytotoxic activity o fNK cells and monocytes," International Journal of Cancer, Mar. 15, 1983 (Mar. 15, 1983) vol. 31, No. 3, pp. 285-289.
Ouichi, "Antibody delivery—from basics to clinical test—Clinical development of antibody-drug conjugate," Drug Deliv. Sys. 28(5):424-429 (2013).
Parikh et al., "The vascular endothelial growth factor family and its receptors", Hematol. Oncol. Clin. N. Am., 2004, 18, pp. 951-971.
Park et al., "Anti-HER2 Immunoliposomes: Enhanced Efficacy Attributes to Targeted Delivery", Clin. Cancer Res., 2002, 8, pp. 1172-1181.
Parker et al., "Targeting CLL Cells Using Rituximab-Conjugated Surface Enhanced Raman Scattering (SERS) Gold Nanoparticles," Blood vol. 116, No. 21, Nov. 1, 2010, pp. 1109.
Perez et al., "Phase 2 Trial of Carboplatin, Weekly Paclitaxel, Biweekly Bevacizumab in Patients with Unresectable Stage IV Melanoma", Cancer, 2009, vol. 115, Issue 1, pp. 119-127.
Petrelli et al., "Targeted Delivery for Breast Cancer Therapy: the History of Nanoparticle-Albumin-Bound Paclitaxxel," Expert Opinion on Pharmacotherapy, Jun. 1, 2010 (Jun. 1, 2010), vol. 11, pp. 1413-1432.
Pikal., "Freeze-drying of proteins, Part II: Formulation selection", Biopharm, 1990, 9, pp. 26-30.
Polak et al., "Mechanisms of local immunosuppression in cutaneous melanoma", Br J Cancer, 2007, 96(12), pp. 1879-1887.
Porrata et al., "Early lymphocyte recovery predicts superior survival after autologous hematopoietic stem cell transplantation in multiple myeloma or non-Hodgkin lymphoma", Blood, 2001, 98(3), pp. 579-585.
Porrata et al., "Timely reconstitution of Immune competence affects clinical outcome following autologous stem cell transplantation", Clin Exp Med., 2004, 4(2):78-85.
Powell et al., "Adoptive transfer of vaccine-induced peripheral blood mononuclear cells to patients with metastatic melanoma following lymphodepletion", J immunol., 2006, 177(9), pp. 6527-6539.
Pries et al., "Cytokines in head and neck cancer", Cytokine Growth Factor Rev., 2006, 17(3), pp. 141-146.
Ranieri et al., "Vascular endothelial growth factor (VEGF) as a taget of bevacizumab in cancer: from the biology to the clinic", Curr. Med. Chem., 2006, 13, 1845-1857.
Rao et al., "Combination of Paclitaxxel and Carboplatin as Second-Line Therapy for Patients with Metastatic Melanoma", Cancer, Jan. 15, 2006, vol. 106, No. 2, pp. 375-382.
Ribas et al., "Antitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.
Rosenberg et al., "Tumor progression can occur despite the induction of very high levels of self/tumor antigen-specific CD8+ T cells in patients with melanoma", J. Immunol., 2005, 175(9), pp. 6169-6176.
Roy et al., "Tumor associated release of interluekin-10 alters the prolactin receptor and down—regulates prolactin responsiveness of Immature cortical thymocytes", J Neuroimmunol., 2007, 186(1-2), pp. 112-120.
Rudikoff et al., "Single amino acid substitution altering antigen-binding specificity," Proc Natl Acad Sci USA 1982 vol. 79 pp. 1979-1983.
Rudnicka et al., "Rituximab causes a polarization of B cells that augments its therapeutic function in NK-cell-mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets. 2015, 15(1):71-86.
Salven et al., "Enhanced expression of vascular endothelial growth factor in metastatic melanoma", Br. J. Cancer, 1997, 76(7), pp. 930-934.
Sandler et al., "Paclitaxel-carboplatin alone or with bevacizumab for non-small-cell lung cancer", N. Engl. J. Med., 2006, 355:2542-2550.
Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.
Schrama et al. "Antibody targeted drugs as cancer therapeutics", Nature Review 5:147-159 (2006).
Sester et al., "Differences in CMV-specific T-cell levels and long-term susceptibility to CMV infection after kidney, heart and lung transplantation", Am J Transplant., 5(6):1483-1489, Jun. 2005.
Soda et al., "Latest topics of new medicine Albumin-bound paclitaxel," Mol. Respiratory Dis. 17(1):100-103 (Mar. 1, 2013).
Srivastava et al., "Angiogenesis in cutaneous melanoma: pathogenesis and clinical implications", Microsc. Res. Tech., 2003, 60:208-224.
Stancovski et al., "Mechanistic aspects of the opposing effects of monoclonal antivodies to the ERBB2 receptor on tumor growth," Proc Natl Acad Sci USA, 88: 8691-8695, (1991).
Streit et al., "Angiogenesis, lymphangiogenesis, and melanoma metastasis", Oncogene, 2003, 22, pp. 3172-3179.
Taieb et al., "Chemoimmunotherapy of tumors: Cyclophosphamide synergitzes with exoxome based vaccines", J. Immunol., Mar. 1, 2006, 176(5):2722-2729.
Tao et al., "Inhibiting the growth of malignant melanoma by blocking the expressioni of vascular endothelial growth factor using an RNA interference approach", Br. J. Dermatol., 2005, 153:715-724.
Tas et al., "Circulating serum levels of angiogenic factors and vascular endothelial growth factor receptors 1 and 2 in melanoma patients", Melanoma Res., 2006, 16:405-411.
Terheyden et al., "Anti-vascular endothelial growth factor antibody bevacizumab in conjunction with chemotherapy in metastasizing melanoma", J Cancer Res Clin Oncol, 2007, 133(11), pp. 897-901.
Terui, English Translation of Molecular-Targeted Therapy for Cancer: Progresses and Challenges, "Daratumumab, Antibody Drug against Myeloma", Pharma Med., Nov. 10, 2013, vol. 31, No. 11, p. 27-30.
Ugurel et al., "Increased serum concentration of angiogenic factors in malignant melanoma patients correlates with tumor progression and survival", J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.
Venice et al., "Circulating tumor antigen-specific regulatory T cells in patients with metstatic melanoma", Proc Natl Acad Sci USA, 2007, 104(52), pp. 20884-20889.

(56) References Cited

OTHER PUBLICATIONS

Vishnu et al., "Safety and Efficacy of nab-Paclitaxel in the Treatment of Patients with Breast cancer," Breast Cancer: Basic and Clinical Research, 2011, vol. 5, pp. 53-65.
Volk et al., "Nab-paclitaxel efficacy in the orthotopic model of human breast cancer is significantly enhanced by concurrent anti-vascular endothelial growth factor A therapy," Neoplasia 10(6):613-623 (2006).
Volk-Draper et al, "Novel Model for Basaloid Triple-negative Breast Cancer: Behavior In Vivo and Response to Therapy", vol. 14, No. 10, Oct. 1, 2012, 18 pages.
Wagner et al., "Enhanced drug targeting by attachment of an anti alphav integrin antibody to doxorubicin loaded human serum albumin nanoparticles", Biomaterials., 31(8):2388-2398, Epub Dec. 23, 2009.
Walker et al., "Monitoring immune responses in cancer patients receiving tumor vaccines", Int Rev Immunol., 2003, 22(3-4):283-319.
Wang et al., "Biofunctionalized targeted nanoparticles for therapeutic applications", Expert Opln. Biol. Ther., 2008, 8 (8):1063-1070.
Wang et al., "Paclitaxel at ultra low concentrations inhibits angiogenesis without affecting cellular microtubule assembly", Anti-Cancer Drugs, 2003, vol. 14, Issue 1, pp. 13-19.
Washington University School of Medicine "Phase I/II Study of Abraxane in Recurrent and Refractory Lymphoma", ClinicalTrials.gov, Dec. 6, 2016, 7 pages.
Weber, "Review: anti-CTLA-4 antibody ipilimumab: case studies of clinical response and immune-related adverse events", Oncologist, Jul. 2007, 12(7), pp. 864-872.
Wiernik et al., "Phase I trial of taxol given as a 24-hour infusion every 21 days: responses observed in metastic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19, No. 10, pp. 1223-1234.
Wu et al., "Aptamers: Active Targeting Ligands for Cancer Diagnosis and Therapy", Theranostics, 2015, 5(4):322-344.
Yardley et al., "A pilot studyd of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee et al., "Adoptive T cell therapy using antigen-specific CD8+ T cell clones for the treatment of patients with metastatic melanoma: In vivo persistance, migration, and antitumor effect of transferred T cells", Proc Natl Acad Sci USA, 2002, 99(25):16168-16173.
Yu et al., "Interaction between bevacizumab and murine VEGF-A: a reassessment," Invest. Ophtalmol. Visual Sci. 49 (2): 522-527, Feb. 2008.
Yuan et al., "Vascular Permeability in a Human Tumor Xenograft: Molecular Size Dependence and Cutoff Size", Cancer Research, Sep. 1, 1995, 55, pp. 3752-3756.
Yuan et al., "Time-dependent vascular regression and permeability changes in established human tumor xenografts induced by an anti-vascular endothelial growth factor/vascular permeability factor antibody," Proc. Natl. Acad. Sci. USA 93(25):14765-14770 (1996).
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13-531-536.
Anonymous, "Phase I/II Study of Abraxane in Recurrent and Refractory Lymphoma", NCT01555853, ClinicalTrials.gov, Jun. 6, 2014 (8 pages).
U.S. Appl. No. 15/092,403, office action dated May 23, 2019.
U.S. Appl. No. 15/092,433, office action dated May 30, 2019.
U.S. Appl. No. 15/412,581, office action dated Mar. 8, 2019.
U.S. Appl. No. 15/412,610, office action dated Mar. 14, 2019.
U.S. Appl. No. 15/414,526; office action dated Mar. 12, 2019.
U.S. Appl. No. 15/414,533; office action dated Mar. 8, 2019.
U.S. Appl. No. 15/430,411, office action dated May 1, 2019.
U.S. Appl. No. 15/452,669; office action dated Jun. 24, 2019.
U.S. Appl. No. 15/456,377; office action dated Mar. 19, 2019.
U.S. Appl. No. 15/456,377; office action dated Jul. 5, 2019.
U.S. Appl. No. 15/456,382; office action dated Jul. 8, 2019.
U.S. Appl. No. 15/456,395; office action dated Mar. 28, 2019.
U.S. Appl. No. 15/456,399; office action dated Mar. 28, 2019.
U.S. Appl. No. 15/456,382; office action dated Mar. 18, 2019.
U.S. Appl. No. 15/456,391; office action dated Mar. 15, 2019.
U.S. Appl. No. 15/460,552; office action dated Apr. 1, 2019.
U.S. Appl. No. 15/460,699; office action dated Mar. 28, 2019.
U.S. Appl. No. 15/461,288; office action dated Apr. 1, 2019.
Bedu-Addo "Understanding Lyophilization Formulation Development", Pharmaceutical Technology Lyophilization. pp. 10-18 (2004).
Beers et al. "CD20 as a Target for Therapeutic Type I and II Monoclonal Antibodies", Seminars in Hematology 47 (2):107-114 (2010).
Cheng et al. Molecularly targeted drugs for metaastic colorectal cancer. Drug Des Devel Ther. Nov. 1, 2013; 7:1315-22 (Year: 2013).
Coiffier "The Role of Rituximab in Lymphomas", Rev. Bras. Hematol. Hemoter., 2002, vol. 24, No. 3, ISSN: 1516-8484 (6 pages).
Edwards et al. "The Remarkable Flexibility of the Human Antibody Repertoire; Isolation of Over One Thousand Different Antibodies to a Single Protein, BLyS", J. Mol. Biol 334:103-118 (2003).
European Application No. 16837869.3, Extended European Search Report dated Apr. 4, 2019.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report on Patentability for Application No. PCT/US2017/050137, dated Mar. 21, 2019.
International Search Report and Written Opinion for Application No. PCT/US2017/023442, dated Jun. 16, 2017.
International Search Report and Written Opinioni for Application No. PCT/US2017/023443, dated Jul. 11, 2017.
Iqbal et al. Anti-Cancer Actions of Denosumab. Curr Osteoporos Rep. Dec. 2011; 9(4):173-6. (Year: 2011).
Matthay et al. Promising therapeutic targets in neuroblastoma. Clin Cancer Res. May 15, 2012;18(10):2740-53. (Year: 2012).
Package Insert, Campath® (ALEMTUZUMAB), Millennium and ILEX Partners, LP, 13 pages, available May 2001.
Reck et al. "Ipilimumab in combination with paclitaxel and carboplatin as first-line therapy in extensive-disease-small-cell lung cancer results from a randomized, double-blind, multicenter phase 2 trial", Ann Oncol. 24(1):75-83 (2013).
Robak, T. Emerging monoclonal antibodies and related agents for the treatment of chronic lymphocytic leukemia. Future Oneal. Jan. 2013;9(1):69-91. Abstract Only. (Year: 2013).
Verma et al. "Effect of surface properties on nanoparticle-cell interactions", Small. 6(1):12-21. (2010).
Desai et al., "Enhanced antitumor activity and safely of albumin-bound nab-docetaxel versus polysorbate 80-based docetaxel", Eur. J. Cancer, Suppl.; 18th Symposium on molecular targets and cancer therapeutics; Prague, Czech Republic; Nov. 7-10, 2006, vol. 4, No. 12, Nov. 2006 2006-11), p. 49.
Flores et al., "Novel oral taxane therapies: recent Phase 1 results", Clin. Invest, vol. 3, No. 4, Apr. 1, 2013 (Apr. 1, 2013), pp. 333-341, XP055426571, UK, ISSN: 2041-6792. DOI: 10.4155/cl.13.18.
Hassan et al.: "Comparison of different crosslinking methods for prepration of docetaxel-loaded albumin nanoparticles," Iranian J. Pharm. Res. vol. 14, No. 2, Apr. 2015 (Apr. 2015), pp. 385-394.
Jin et al.: "Docetaxel-loaded PEG-albumin nanopartides with improved antitumor efficiency against non-small cell lung cancer", Oncology Rep., nov. 36, No. 2, Aug. 8, 2016 (Aug. 8, 2016), pp. 871-876, XP055425487, ISSN: 1021-335X, DOI: 10.3892/or.2016.4863.
Qu Na et al., "Cabazitaxel-loaded human serum albumin nanoparticles as a therapeutic agent against prostate cancer", Intl. J. Nanomed., vol. 11, Jul. 26, 2016 (Jul. 26, 2016), pp. 3451-3459.

(56) References Cited

OTHER PUBLICATIONS

Samaranayake et al., "Modified taxols. 5.1 Reaction of taxol with electrophilic reagents and preparation of a rearranged taxol derivative with tubulin assembly activity", J. Org, Chem., vol. 56, 1991, pp. 5114-5119.
International Search Report and Written Opinion for Application No. PCT/US2017/050355 dated Jan. 30, 2018.
Anoymous "Paclitaxel Albumin-Stabilized Nanoparticle Formulation and Bevacizumab in Treating Patients With Stage IV Melanoma That Cannot Be Removed by Surgery or Gynecological Cancers", NCT02020707, ClinicafTrials.gov, Dec. 25, 2013 (13 pages).
U.S. Appl. No. 15/187,672, office action dated Sep. 11, 2019.
U.S. Appl. No. 15/225,428, office action dated Dec. 6, 2019.
U.S. Appl. No. 15/225,542, office action dated Jan. 14, 2020.
U.S. Appl. No. 15/359,569, office action dated Jan. 17, 2020.
U.S. Appl. No. 15/430,411; office action dated Oct. 31, 2019.
U.S. Appl. No. 15/675,596; office action dated Dec. 3, 2019.
U.S. Appl. No. 15/752,155; office action dated Sep. 25, 2019.
Cirstoiu-Hapca et al. "Benefit of anti-HER2-coated paclitaxel-loaded immuno-nanpoarticles in the treatment of disseminated ovarian cancer: Therapeutic efficacy and biodistribution in mice", Journal of Controlled Release 144:324-331 (2010).
European Application No. 17771005.0, Extended European Search Report dated Oct. 17, 2019.
European Application No. 17771006.8, Extended European Search Report dated Oct. 10, 2019.
Liu et al. "Freeze-Drying of Proteins". In: Walkers W., Oldenhof H. (eds) Cryopreservation and Freeze-Drying Protocols. Methods in Molecular Biology (Methods and Protocols), vol. 1257. Springer, New York, NY; published online Nov. 14, 2014.
Reynolds et al. "Phase II Trial of Nanoparticle Albumin-Bound Paclitaxel, Carboplatin, and Bevacizumab in First-Line Patients with Advanced Nonsquamous Non-small Cell Lung Cancer", J Thoracic Oncology 4(12):1537-1543 (2009).
U.S. Appl. No. 15/286,024, office action dated Feb. 10, 2020.
U.S. Appl. No. 15/430,411, office action dated Apr. 17, 2020.
U.S. Appl. No. 15/452,669; office action dated Mar. 3, 2020.
U.S. Appl. No. 15/456,377; office action dated Mar. 12, 2020.
U.S. Appl. No. 15/456,391; office action dated Feb. 4, 2020.
U.S. Appl. No. 15/460,699; office action dated Mar. 3, 2020.
U.S. Appl. No. 15/461,288; office action dated Feb. 28, 2020.
U.S. Appl. No. 15/752,155; office action dated Feb. 7, 2020.
European Application No. 17750912.2 Extended European Search Report dated Jan. 2, 2020.
Miele et al. "Albumin-bound formulation of paclitaxel (Abraxane® ABI-007) in the treatment of breast cancer", International Journal of Nanomedicine 4:99-105 (2009).
Warner et al. "Alemtuzumab use in relapsed and refractory chronic lymphocytic leukemia: a history and discussion of future rational use", Ther Adv Hematol 3(6):375-389 (2012).
Zhao et al. "Abraxane, the Nanoparticle Formulation of Paclitaxel Can Induce Drug Resistance by Ip-Regulation of P-gp", PLoS One 10(7):e0131429 (2015) (19 pages).
"U.S. Appl. No. 15/225,542; office action dated Jul. 30, 2020".
"U.S. Appl. No. 15/286,024, office action dated Jul. 29, 2020".
"U.S. Appl. No. 15/359,569; office action dated Aug. 10, 2020".
"U.S. Appl. No. 15/452,669; office action dated Oct. 21, 2020".
"U.S. Appl. No. 15/456,377; office action dated Sep. 1, 2020".
"U.S. Appl. No. 15/675,596; office action dated May 28, 2020".
"U.S. Appl. No. 15/675,596; office action dated Oct. 20, 2020".
"U.S. Appl. No. 16/086,977; office action dated Sep. 3, 2020".
Beth A. Weaver entitled "How Taxol/paclitaxel kills cancer cells" published in Molecular Biology of the Cell, vol. 25, pp. 2677-2681, Sep. 15, 2014, Sep. 15, 2014.
V.N. Kapoor and N. Mahindroo entitled "Recent advances in structure modifications of Taxol (Paclitaxel)" in Indian Journal Chemistry vol. 36B, pp. 639-652, published Aug. 1997, Aug. 1997.
D.I. Kingston entitled "A Natural Love of Natural Products" in Journal of Organic Chemistry vol. 73, pp. 3975-3984, published Jun. 6, 2008.
Office Action for Indonesian Application No. PID201902404 dated Mar. 18, 2021 (translated), 5 pages.
Office Action for Russian Application No. 2019110070 dated Mar. 3, 2021 (with translation), 15 pages, Mar. 3, 2021.
Kharkevich D.A. Pharmacology: Textbook, 2010, 10th edition, pp. 72-82, 2010.
Samaranayake G. et al., "Modified taxols. 5. Reaction of taxol with electrophilic reagents and preparation of a rearranged taxol derivative with tubulin assembly activity", Journal of Organic Chemistry, 1991, vol. 56, pp. 5114-5119, Received May 15, 1990, May 15, 1990.
Office Action for Japanese Patent Application No. 2019-512649 dated Sep. 8, 2021, 9 pages (with Translation).
First Office Action for Chinese Application No. 201780066304.X dated Dec. 2, 2021 (with translation), 28 pages.

* cited by examiner

Paclitaxel

20-Acetoxy-4-deactyl-5-epi-20, O-secotaxol
(The Meerwein Product of Paclitaxel)

NTP Mean: 134.4 +/- 7.2 nm

NTP + 4mg/ml Bev
Mean: 133.1 +/- 7.1

NTP + 6 mg/ml Bev
Mean: 146.0 +/- 5.0 nm

NTP + 8 mg/ml Bev
Mean: 141.1 +/- 2.3 nm

NTP + 10 mg/ml Bev
Mean: 151.1 +/- 2.7 nm

Isotype control

Anti-CD20

PACLITAXEL-ALBUMIN-BINDING AGENT COMPOSITIONS AND METHODS FOR USING AND MAKING THE SAME

CROSS REFERENCE TO RELATED APPLICATIONS

This application is a 35 U.S.C. § 371 national phase application of PCT Application PCT/US2017/050355 filed Sep. 6, 2017, which claims the benefit of the priority date of U.S. Provisional Application No. 62/384,119, filed Sep. 6, 2016; the entire, contents of each of which are incorporated by reference herein in its entirety.

FIELD OF THE INVENTION

This application relates to novel compositions of binding agents and carrier proteins and methods of making and using the same, in particular, as a cancer therapeutic.

BACKGROUND

Chemotherapy remains a mainstay for systemic therapy for many types of cancer, including melanoma. Most chemotherapeutic agents are only slightly selective to tumor cells, and toxicity to healthy proliferating cells can be high (Allen T M. (2002) *Cancer* 2:750-763), often requiring dose reduction and even discontinuation of treatment. In theory, one way to overcome chemotherapy toxicity issues as well as improve drug efficacy is to target the chemotherapy drug to the tumor using antibodies that are specific for proteins selectively expressed (or overexpressed) by cancer cells to attract targeted drugs to the tumor, thereby altering the biodistribution of the chemotherapy and resulting in more drug going to the tumor and less affecting healthy tissue. Despite 30 years of research, however, specific targeting rarely succeeds in the therapeutic context.

Conventional antibody dependent chemotherapy (ADC) is designed with a toxic agent linked to a targeting antibody via a synthetic protease-cleavable linker. The efficacy of such ADC therapy is dependent on the ability of the target cell to bind to the antibody, the linker to be cleaved, and the uptake of the toxic agent into the target cell. Schrama, D. et al. (2006) *Nature reviews. Drug discovery* 5:147-159.

Antibody-targeted chemotherapy promised advantages over conventional therapy because it provides combinations of targeting ability, multiple cytotoxic agents, and improved therapeutic capacity with potentially less toxicity. Despite extensive research, clinically effective antibody-targeted chemotherapy remains elusive: major hurdles include the instability of the linkers between the antibody and chemotherapy drug, reduced tumor toxicity of the chemotherapeutic agent when bound to the antibody, and the inability of the conjugate to bind and enter tumor cells. In addition, these therapies did not allow for control over the size of the antibody-drug conjugates.

There remains a need in the art for antibody-based cancer therapeutics that retain cytotoxic effect for targeted drug delivery to provide reliable and improved anti-tumor efficacy over prior therapeutics.

SUMMARY

According to the present invention are disclosed nanoparticles which contain (a) carrier protein, (b) optionally a binding agent, and (c) paclitaxel, wherein the paclitaxel is present in an amount that is less than an amount that provides a therapeutic effect, and optionally (d) a therapeutic agent. Some aspects of the current invention are predicated, in part, on the idea that a reduced amount of paclitaxel, for example compared to that in albumin-bound nanoparticles such as ABRAXANE®, facilitates the formation of a complex of a carrier protein, such as albumin, with a binding agent, such as an antibody, to provide a stable nanoparticle. These nanoparticles may be referred to herein as "reduced toxicity nanoparticles" (RTP) or RTP complexes.

Also disclosed herein are nanoparticles which contain (a) carrier protein, (b) a paclitaxel derivative, the paclitaxel derivative having reduced toxicity compared to paclitaxel, and optionally (c) a binding agent and/or (d) a therapeutic agent.

Further described herein are nanoparticle compositions, and methods of making and using the nanoparticles.

In one aspect is provided a nanoparticle comprising albumin and a paclitaxel derivative, wherein the paclitaxel derivative is less toxic than paclitaxel. In one embodiment, the paclitaxel derivative is a Meerwein Product of Paclitaxel. In a preferred embodiment, the paclitaxel derivative is 20-acetoxy-4-deactyl-5-epi-20, O-secotaxol. In one embodiment, the paclitaxel derivative is Baccatin III ((2β,5α,7α,10α,13β)-4,10-Diacetoxy-1,7,13-trihydroxy-9-oxo-5,20-epoxytax-11-en-2-yl benzoate). In one embodiment, the nanoparticle is held together by non-covalent bonds between the albumin and the paclitaxel derivative. In one embodiment, the albumin and the paclitaxel derivative have a relative weight ratio of less than about 10:1. In one embodiment, the nanoparticles do not comprise paclitaxel.

In one embodiment is provided a nanoparticle complex comprising albumin and a paclitaxel derivative, and further comprises binding agents (e.g., antibodies) having an antigen-binding domain. In one embodiment, an amount of the binding agents (e.g., antibodies) are arranged on an outside surface of the nanoparticle complexes. In some embodiments, the binding agents are a substantially single layer of binding agents on all or part of the surface of the nanoparticle. In one embodiment, the binding agents are bound to the carrier protein by non-covalent bonds. Preferably, the binding agents are antibodies.

In one embodiment, the nanoparticle complex further comprises a therapeutic agent. In one embodiment, the therapeutic agent is abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, or cyclophosphamide. In one embodiment, the therapeutic agent is an agent listed in Table 2.

In one aspect is provided a nanoparticle composition comprising the nanoparticles or nanoparticle complexes as described herein.

In one aspect is provided a nanoparticle comprising a carrier protein (e.g., albumin) and paclitaxel, wherein the paclitaxel is present in an amount that is less than an amount that provides a therapeutic effect. In one embodiment, the nanoparticle is held together by non-covalent bonds between the carrier protein and the paclitaxel. In one aspect, the nanoparticle complex was made by combining the carrier protein (e.g., albumin) and paclitaxel at a relative weight ratio of greater than about 10:1 carrier protein to paclitaxel.

In one embodiment, the amount of paclitaxel present in the nanoparticles (nanoparticle complexes) or nanoparticle composition is greater than or equal to a minimum amount capable of providing stability to the nanoparticle complexes comprising a protein carrier (e.g., albumin) and paclitaxel. In one embodiment, the amount of paclitaxel present in the nanoparticles or nanoparticle composition is greater than or equal to a minimum amount capable of providing affinity of the paclitaxel with the protein carrier (e.g., albumin). In one embodiment, the amount of paclitaxel present in the nanoparticles or nanoparticle composition is greater than or equal to a minimum amount capable of facilitating complex formation of the paclitaxel and the protein carrier (e.g., albumin).

The ratio of albumin to paclitaxel in the nanoparticles or nanoparticle composition preferably is less than that present in ABRAXANE®. ABRAXANE® contains 100 mg paclitaxel for about 900 mg albumin. In one embodiment, the weight ratio of the carrier protein (e.g., albumin) to paclitaxel in the nanoparticle composition is greater than about 9:1. In one embodiment, the weight ratio is greater than about 10:1, or 11:1, or 12:1, or 13:1, or 14:1, or 15:1, or about 16:1, or about 17:1, or about 18:1, or about 19:1, or about 20:1, or about 21:1, or about 22:1, or about 23:1, or about 24:1, or about 25:1, or about 26:1, or about 27:1, or about 28:1, or about 29:1, or about 30:1. In one embodiment, the weight ratio of the carrier protein to paclitaxel in the nanoparticle complex is greater than about 9:1. In one embodiment, the weight ratio is greater than about 10:1, or 11:1, or 12:1, or 13:1, or 14:1, or 15:1, or about 16:1, or about 17:1, or about 18:1, or about 19:1, or about 20:1, or about 21:1, or about 22:1, or about 23:1, or about 24:1, or about 25:1, or about 26:1, or about 27:1, or about 28:1, or about 29:1, or about 30:1.

In one embodiment, the amount of paclitaxel is greater than or equal to a minimum amount capable of providing stability to the nanoparticle complexes comprising a protein carrier (e.g., albumin) and paclitaxel, and optionally at least one therapeutic agent. In one embodiment, the amount of paclitaxel is greater than or equal to a minimum amount capable of providing affinity of the at least one therapeutic agent to the protein carrier. In one embodiment, the amount of paclitaxel is greater than or equal to a minimum amount capable of facilitating complex formation of the at least one therapeutic agent and the protein carrier.

In any of the embodiments, the amount of paclitaxel can be less than a therapeutic amount for paclitaxel. In other words, the amount can be less than what is provided or contemplated for providing a therapeutic benefit, such as for example, a chemotherapeutic amount to effectively treat a cancer.

In one embodiment, the amount of paclitaxel present in the nanoparticle composition is less than about 5 mg/mL. In one embodiment, the amount of paclitaxel present in the nanoparticle composition is less than about 4.54 mg/mL, or about 4.16 mg/mL, or about 3.57 mg/mL, or about 3.33 mg/mL, or about 3.12 mg/mL, or about 2.94 mg/mL, or about 2.78 mg/mL, or about 2.63 mg/mL, or about 2.5 mg/mL, or about 2.38 mg/mL, or about 2.27 mg/mL, or about 2.17 mg/mL, or about 2.08 mg/mL, or about 2 mg/mL, or about 1.92 mg/mL, or about 1.85 mg/mL, or about 1.78 mg/mL, or about 1.72 mg/mL, or about 1.67 mg/mL.

Without being bound by theory, it is contemplated that binding to the carrier protein, e.g., complexation of the binding agent to the carrier protein, occurs through an albumin-binding motif on the binding agents and/or an antibody-binding motif on the carrier protein. In one embodiment, the binding agent comprises an albumin-binding motif. In one embodiment, the carrier protein comprises an antibody-binding motif. Non-limiting examples of antibody-binding motifs can be found in PCT Application No. PCT/US2017/045643, filed Aug. 4, 2017, which is incorporated herein by reference in its entirety. In some embodiments, the binding agent is a non-therapeutic and non-endogenous human antibody, a fusion protein, e.g., fusion of an antibody Fc domain to a peptide that binds a target antigen, or an aptamer.

In one embodiment, the binding agent comprises an antigen-binding domain. In one embodiment, the antigen is CD3, CD19, CD20, CD38, CD30, CD33, CD52, PD-1, PD-L1, PD-L2, CTLA-4, RANK-L, GD-2, Ly6E, HER3, EGFR, DAF, ERBB-3 receptor, CSF-1R, HER2, STEAP1, CD3, CEA, CD40, OX40, Ang2-VEGF, or VEGF.

Tin one embodiment, the binding agent is an antibody selected from ado-trastuzumab emtansine, alemtuzumab, atezolizumab, bevacizumab, cetuximab, denosumab, dinutuximab, ipilimumab, nivolumab, obinutuzumab, ofatumumab, panitumumab, pembrolizumab, pertuzumab, rituximab, Ramucirumab, avelumab or durvalumab, pidilizumab, BMS 936559, OKT3, and trastuzumab.

The invention further includes lyophilized nanoparticles and nanoparticle compositions, and lyophilized nanoparticles and compositions that do not materially differ from, or are the same as, the properties of freshly-prepared nanoparticles. In particular, the lypholized composition, upon resuspending in aqueous solution, is similar or identical to the fresh composition in terms of particle size, particle size distribution, toxicity for cancer cells, binding agent affinity, and binding agent specificity. Surprisingly, lyophilized nanoparticles retain the properties of freshly-made nanoparticles after resuspension, notwithstanding the presence of two different protein components in these particles. In one embodiment, the lyophilized composition is stable at room temperature for at least about 3 months, 4 months, 5 months, 6 months, 7 months, 8 months, 9 months, 10 months, 11 months, 12 months, or longer. In one embodiment, the lyophilized composition is stable at room temperature for at least 3 months. In one embodiment, the reconstituted nanoparticles retain the activity of the therapeutic agent and are capable of binding to the target in vivo.

In some embodiments, the at least one therapeutic agent is located inside the nanoparticle. In other embodiments, the at least one therapeutic agent is located on the outside surface of the nanoparticle. In yet other embodiments, the at least one therapeutic agent is located inside the nanoparticle and on the outside surface of the nanoparticle.

In some embodiments, the nanoparticle contains more than one type of therapeutic agent. For example, a taxane and a platinum drug, e.g. paclitaxel and cisplatin.

In some embodiments, the nanoparticle further comprises at least one additional therapeutic agent that is not paclitaxel. In some embodiments, the at least one therapeutic agent is abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, or cyclophosphamide.

In some embodiments, the binding agents, carrier protein and/or, when present, therapeutic agent, are bound through non-covalent bonds.

In some embodiments, the carrier protein is selected from the group consisting of gelatin, elastin, gliadin, legumin, zein, a soy protein, a milk protein, and a whey protein. In preferred embodiments, the carrier protein is albumin, for example, human serum albumin.

In some embodiments, the composition is formulated for intravenous delivery. In other embodiments, the composition is formulated for direct injection or perfusion into a tumor.

In some embodiments, the nanoparticles have a dissociation constant between about $1\times10^{-11}$ M and about $1\times10^{-9}$ M.

In one embodiment, provided herein are methods of making the nanoparticle compositions, wherein said method comprises contacting the carrier protein and the paclitaxel and the at least one therapeutic agent under conditions and ratios of components that will allow for formation of the desired nanoparticles.

In some aspects, provided herein are methods for forming an albumin-paclitaxel derivative or albumin-paclitaxel nanoparticle, wherein method comprises: homogenizing the albumin with paclitaxel derivative or paclitaxel in a solution under high pressure, to generate an albumin-paclitaxel derivative or albumin-paclitaxel nanoparticle.

In some aspects, provided herein are methods of making nanoparticle compositions, wherein said methods comprise contacting the carrier protein, the paclitaxel, and/or the therapeutic agent with the binding agents in a solution having a pH of between 5.0 and 7.5 and a temperature between about 5° C. and about 60° C., between about 23° C. and about 60° C., or between about 55° C. and about 60° C. under conditions and ratios of components that will allow for formation of the desired nanoparticles. In one embodiment, the nanoparticle is made between 55° C. and 60° C. and pH 7.0. In another aspect, provided herein are methods of making the nanoparticle compositions, wherein said method comprises (a) contacting the carrier protein, the paclitaxel and the therapeutic agent to form a core and (b) optionally contacting the core with the antibodies in a solution having a pH of about 5.0 to about 7.5 at a temperature between about 5° C. and about 60° C., between about 23° C. and about 60° C., or between about 55° C. and about 60° C. under conditions and ratios of components that will allow for formation of the desired nanoparticles.

In some aspects, an amount of a therapeutic agent (e.g., a therapeutic agent which is not paclitaxel) can also be added to the carrier protein.

In further embodiments, the nanoparticles are made as above, and then lyophilized.

In another aspect, provided herein are methods for treating a cancer cell, the method comprising contacting the cell with an effective amount of a nanoparticle composition disclosed herein to treat the cancer cell.

In one embodiment is provided a method for killing cancer cells in a population of cancer cells, the method comprising contacting the cells with an effective amount of a nanoparticle composition, wherein said composition is maintained in contact with said cells for a sufficient period of time to kill cancer cells, wherein said nanoparticle composition comprises nanoparticle complexes, each of the nanoparticles comprising albumin and paclitaxel, wherein the paclitaxel is present in an amount that is less than an amount that provides a therapeutic effect.

In one embodiment is provided a method for treating cancer in patient in need thereof, the method comprising administering to the patient a nanoparticle composition comprising nanoparticle complexes, each of the nanoparticles comprising albumin and paclitaxel, wherein the paclitaxel is present in an amount that is less than an amount that provides a therapeutic effect.

In another aspect, provided herein are methods for treating a tumor in a patient in need thereof, the method comprising contacting the cell with an effective amount of a nanoparticle composition disclosed herein to treat the tumor. In some embodiments, the size of the tumor is reduced. In other embodiments, the nanoparticle composition is administered intravenously. In yet other embodiments, the nanoparticle composition is administered by direct injection or perfusion into the tumor.

In some embodiments, the methods provided herein include the steps of: a) administering the nanoparticle composition once a week for three weeks; b) ceasing administration of the nanoparticle composition for one week; and c) repeating steps a) and b) as necessary to treat the tumor.

In some embodiments, the therapeutically effective amount comprises about 75 mg/m$^2$ to about 175 mg/m$^2$ of the carrier protein (i.e., milligrams carrier protein per m$^2$ of the patient). In other embodiments, the paclitaxel is of an amount that is less than about 75 mg/m$^2$, such as between 5 mg/m$^2$ and 75 mg/m$^2$. In other embodiments, the paclitaxel is of an amount that is less than a therapeutically effective amount. In some embodiments, the therapeutic agent is of a therapeutically effective amount. In some embodiments, the therapeutically effective amount comprises about 30 mg/m$^2$ to about 70 mg/m$^2$ of the binding agent. In yet other embodiments, the therapeutically effective amount comprises about 30 mg/m$^2$ to about 70 mg/m$^2$ bevacizumab.

An embodiment of the invention includes a method for increasing the duration of tumor uptake of a chemotherapeutic agent by administering the chemotherapeutic agent in a nanoparticle comprising a carrier protein and the chemotherapeutic agent having surface complexation with an antibody, e.g., an antibody that specifically binds to an antigen on or shed by the tumor.

BRIEF DESCRIPTION OF THE DRAWINGS

The following figures are representative only of the invention and are not intended as a limitation. For the sake of consistency, the nanoparticles of this invention using ABRAXANE® and bevacizumab employ the acronym "AB" and the number after AB such as AB160 is meant to confer the average particle size of these nanoparticles (in nanometers). Likewise, when the binding agent is rituximab, the acronym is "AR" while the number thereafter remains the same.

DETAILED DESCRIPTION

Figure 1:
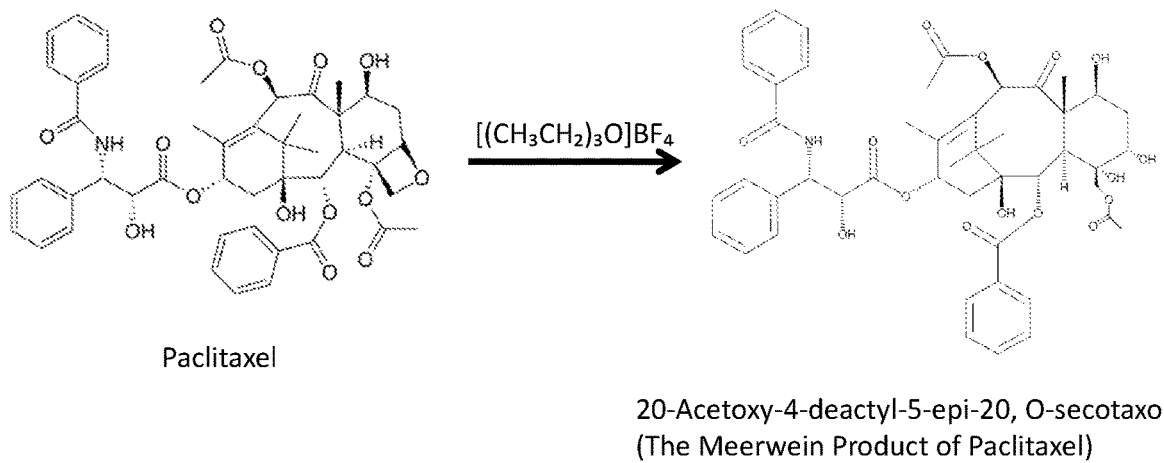
FIG. 1 shows the reaction of paclitaxel with Meerwein's Reagent to form the Meerwein's Product of Paclitaxel (20-Acetoxy-4-deactyl-5-epi-20, O-secotaxol).
Figure 2A:
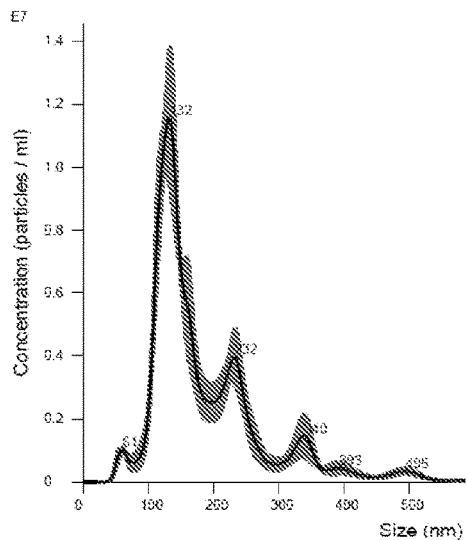
FIGS. 2A-2E show the nanoparticle diameter of non-toxic nanoparticles (NTP) alone (FIG. 2A) or incubated with 4 mg/mL (FIG. 2B), 6 mg/mL (FIG. 2C), 8 mg/mL (FIG. 2D) or 10 mg/mL (FIG. 2E) bevacizumab for 30 min. Diameter was measured at a 1:300 dilution using Malvern Nanosight technology.
Figure 2B:
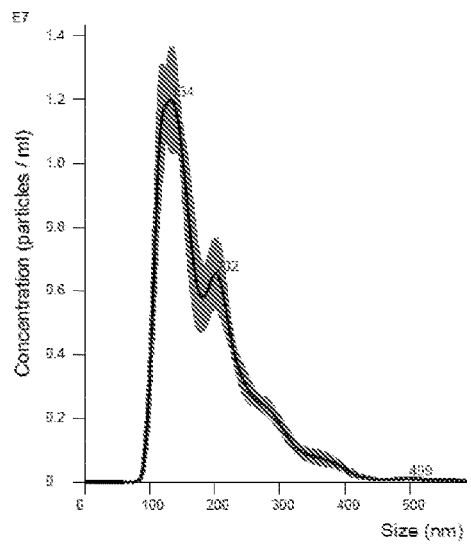
Figure 2C:
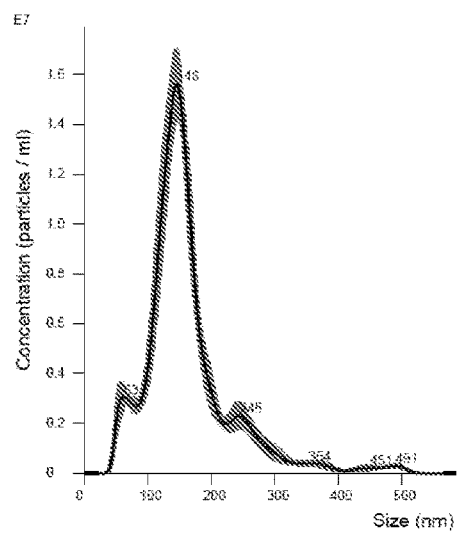
Figure 2D:
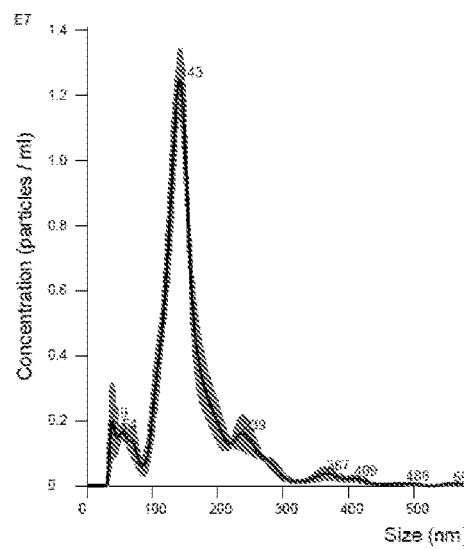
Figure 2E:
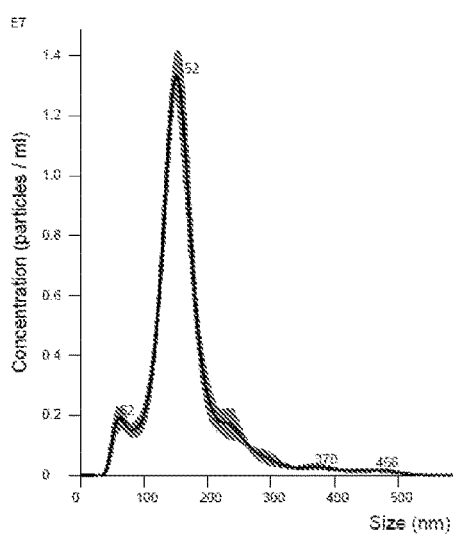

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%,1%, or any subrange or subvalue there between. Preferably, the term "about" when used with regard to a dose amount means that the dose may vary by +/−10%. For example, "about 400 to about 800 binding agents" indicates that an outside surface of a nanoparticles contain an amount of binding agent between 360 and 880 particles.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "nanoparticle" as used herein refers to particles having at least one dimension which is less than 5 microns. In preferred embodiments, such as for intravenous administration, the nanoparticle is less than 1 micron. For direct administration, the nanoparticle is larger. Even larger particles are expressly contemplated by the invention.

In a population of particles, the sizes of individual particles are distributed about a mean. Particle sizes for the population can therefore be represented by an average, and also by percentiles. D50 is the particle size below which 50% of the particles fall. 10% of particles are smaller than the D10 value and 90% of particles are smaller than D90. Where unclear, the "average" size is equivalent to D50. So, for example, AB160 and AR160 refer to nanoparticles having an average size of 160 nanometers.

The term "nanoparticle" may also encompass discrete multimers of smaller unit nanoparticles. For 160 nm nanoparticles, multimers would therefore be approximately 320 nm, 480 nm, 640 nm, 800 nm, 960 nm, 1120 nm, and so on.

The term "carrier protein" as used herein refers to proteins that function to transport binding agents and/or therapeutic agents. The binding agents of the present disclosure can reversibly bind to the carrier proteins. Examples of carrier proteins are discussed in more detail below.

The term "core" as used herein refers to a central or inner portion of the nanoparticle which may be comprised of a carrier protein, a carrier protein and a therapeutic agent, or other agents or combination of agents. In some embodiments, an albumin-binding motif of the binding agent may be associated with the core.

The term "therapeutic agent" as used herein means an agent which is therapeutically useful, e.g., an agent for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, or any combination thereof.

As used herein, the term, "binding agent", "binding agent specific for", or "binding agent that specifically binds" refers to an agent that binds to a target antigen and does not significantly bind to unrelated compounds. Examples of binding agents that can be effectively employed in the disclosed methods include, but are not limited to, lectins, proteins, and antibodies, such as monoclonal antibodies, e.g. humanized monoclonal antibodies, chimeric antibodies, or polyclonal antibodies, or antigen-binding fragments thereof, as well as aptamers, fusion proteins, and aptamers having or fused to an albumin-binding motif. In an embodiment the binding agent is an exogenous antibody. An exogenous antibody is an antibody not naturally produced in a mammal, e.g. in a human, by the mammalian immune system.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., *Eur. J Immunol.* 17, 105 (1987)) and single chains (e.g., Huston et al., *Proc. Natl. Acad. Sci. US.A.*, 85, 5879-5883 (1988) and Bird et al., *Science* 242, 423-426 (1988), which are incorporated herein by reference). (See, generally, Hood et al., *Immunology*, Benjamin, N.Y., 2ND ed. (1984); Harlow and Lane, *Antibodies. A Laboratory Manual*, Cold Spring Harbor Laboratory (1988); Hunkapiller and Hood, *Nature,* 323, 15-16 (1986), which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric. Antibody or antibodies include any biosimilar(s) of the antibodies disclosed herein. Biosimilars, as used herein, refers to a biopharmaceutical which is deemed to be comparable in quality, safety, and efficacy to a reference product marketed by an innovator company (Section 351(i) of the Public Health Service Act (42 U.S.C. 262(i)).

The term "dissociation constant," also referred to as "$K_d$," refers to a quantity expressing the extent to which a particular substance separates into individual components (e.g., the protein carrier, antibody, and a therapeutic agent).

The terms "lyophilized," "lyophilization" and the like as used herein refer to a process by which the material (e.g., nanoparticles) to be dried is first frozen and then the ice or frozen solvent is removed by sublimation in a vacuum environment. An excipient is optionally included in pre-lyophilized formulations to enhance stability of the lyophilized product upon storage. In some embodiments, the nanoparticles can be formed from lyophilized components (carrier protein, paclitaxel, and optionally antibody and/or a therapeutic agent) prior to use as a therapeutic. In other embodiments, the carrier protein and paclitaxel, and optionally a binding agent, e.g., antibody, and/or a therapeutic agent are first combined to facilitate the formation of stable nanoparticles and then lyophilized. The lyophilized sample may further contain additional excipients.

The term "bulking agents" comprise agents that provide the structure of the freeze-dried product. Common examples used for bulking agents include mannitol, glycine, lactose and sucrose. In addition to providing a pharmaceutically elegant cake, bulking agents may also impart useful qualities in regard to modifying the collapse temperature, providing freeze-thaw protection, and enhancing the protein stability over long-term storage. These agents can also serve as tonicity modifiers. In some embodiments, the lyophilized compositions described herein comprise bulking agents. In some embodiments, the lyophilized compositions described herein do not comprise bulking agents.

The term "buffer" encompasses those agents which maintain the solution pH in an acceptable range prior to lyophilization and may include succinate (sodium or potassium), histidine, phosphate (sodium or potassium), Tris(tris (hydroxymethyl)aminomethane), diethanolamine, citrate (sodium) and the like. The buffer of this invention may have a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "cryoprotectants" generally includes agents which provide stability to the protein against freezing-induced stresses, presumably by being preferentially excluded from the protein surface. They may also offer protection during primary and secondary drying, and long-term product storage. Examples are polymers such as dextran and polyethylene glycol; sugars such as sucrose, glucose, trehalose, and lactose; surfactants such as polysorbates; and amino acids such as glycine, arginine, and serine.

The term "lyoprotectant" includes agents that provide stability to the protein during the drying or 'dehydration' process (primary and secondary drying cycles), presumably by providing an amorphous glassy matrix and by binding with the protein through hydrogen bonding, replacing the water molecules that are removed during the drying process. This helps to maintain the protein conformation, minimize protein degradation during the lyophilization cycle and improve the long-term products. Examples include polyols or sugars such as sucrose and trehalose.

The term "pharmaceutical formulation" refers to preparations which are in such form as to permit the active ingredients to be effective, and which contains no additional components that are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation into a solution.

A "stable" formulation is one in which the protein therein essentially retains its physical stability and/or chemical stability and/or biological activity upon storage. For example, various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

The term "epitope" as used herein refers to the portion of an antigen which is recognized by a binding agent, e.g., an antibody. Epitopes include, but are not limited to, a short amino acid sequence or peptide (optionally glycosylated or otherwise modified) enabling a specific interaction with a protein (e.g., an antibody) or ligand. For example, an epitope may be a part of a molecule to which the antigen-binding site of a binding agent attaches.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. In some embodiments "treating" or "treatment" refers to the killing of cancer cells.

The term "kill" or "killing" with respect to a cancer treatment includes any type of manipulation that will directly or indirectly lead to the death of that cancer cell or at least of portion of a population of cancer cells.

The term "aptamer" refers to a nucleic acid molecule that is capable of binding to a target molecule, such as a polypeptide. For example, an aptamer of the invention can specifically bind to e.g., CD20, CD38, CD52, PD-1, PD-L1, PD-L2, Ly6E, HER2, HER3/EGFR DAF, ERBB-3 receptor, CSF-1R, STEAP1, CD3, CEA, CD40, OX40, Ang2-VEGF, and VEGF. The generation of antibodies with a particular binding specificity and the therapeutic use of aptamers are well established in the art. See, e.g., U.S. Pat. Nos. 5,475,096, 5,270,163, 5,582,981, 5,840,867, 6,011,020, 6,051,698, 6,147,204, 6,180,348 and 6,699,843, and the therapeutic efficacy of Macugen® (Eyetech, N.Y.) for treating age-related macular degeneration, each of which is incorporated herein by reference in its entirety.

The term "oligomer" or "oligomeric" or "oligomerized" as used herein refers to oligomers composed of two or more monomers.

Fusion proteins are bioengineered polypeptides that join a protein or fragment thereof (e.g., the crystallizable fragment (Fc) domain of an antibody) with another biologically active agent (e.g., a protein domain, peptide, or nucleic acid or peptide aptamer) to generate a molecule with desired structure—function properties and significant therapeutic potential. The gamma immunoglobulin (IgG) isotype is often used as the basis for generating Fc-fusion proteins because of favorable characteristics such as recruitment of effector function and increased plasma half-life. Given the range of aptamers, both peptide and nucleic acids, that can be used as fusion partners, fusion proteins have numerous biological and pharmaceutical applications.

The term "non-toxic nanoparticles" (NTPs) or "NTP complexes" refers to nanoparticles comprising a carrier protein (e.g., albumin) and a paclitaxel derivative that is less toxic than paclitaxel. Optionally, the NTPs or NTP complexes comprise binding agents (e.g., antibodies) and/or therapeutic agents (e.g., chemotherapeutic agents).

The phrase "less toxic than paclitaxel" refers to paclitaxel derivatives that exhibit reduced toxicity to (e.g., reduced killing of) cells, including cancer cells and normal cells, as compared to paclitaxel. For example, the Meerwein Product of Paclitaxel (20-Acetoxy-4-deactyl-5-epi-20, O-secotaxol) has significantly reduced toxicity, likely due to the breaking of the C-4,C-5 oxetane ring of paclitaxel.

The term "reduced toxicity nanoparticles" (RTPs) or "RTP complexes" refers to nanoparticles comprising a carrier protein (e.g., albumin) and a reduced amount of paclitaxel compared to ABRAXANE® (.g., an albumin:paclitaxel ratio of about 9:1). Optionally, the RTPs or RTP complexes comprise binding agents (e.g., antibodies) and/or therapeutic agents (e.g., chemotherapeutic agents).

Additionally, some terms used in this specification are more specifically defined below.

Overview

ABRAXANE® for Injectable Suspension (paclitaxel protein-bound particles for injectable suspension) is an albumin-bound form of paclitaxel with a mean particle size of approximately 130 nanometers. Paclitaxel can exist in the particles in a non-crystalline, amorphous state. ABRAXANE® can be supplied as, for example, a lyophilized powder for reconstitution with 20 mL of 0.9% Sodium Chloride Injection, USP prior to intravenous infusion. A single-use vial contains 100 mg of paclitaxel and approximately 900 mg of human albumin. Each milliliter (mL) of reconstituted suspension contains 5 mg paclitaxel.

ABRAXANE® nanoparticles are stabilized albumin-bound paclitaxel. The association of the paclitaxel and albumin can be via, for example, hydrophobic interactions. In some examples, the nanoparticle are stable at an average size of 130 nm. It is also known that other hydrophobic drugs such as, for example, docetaxel, rapamycin, can similarly form stabilized nanoparticles by binding to albumin.

For conventional ADCs to be effective, it is critical that the linker be stable enough not to dissociate in the systemic circulation but allow for sufficient drug release at the tumor site. Alley, S. C., et al. (2008) *Bioconjug Chem* 19:759-765. This has proven to be a major hurdle in developing effective drug conjugate (Julien, D. C., et al. (2011) *MAbs* 3:467-478; Alley, S. C., et al. (2008) *Bioconjug Chem* 19:759-765); therefore, an attractive feature of the nano-immune conjugate is that a biochemical linker is not required.

Another shortcoming of current ADCs is that higher drug penetration into the tumor has not been substantively proven in human tumors. Early testing of ADCs in mouse models suggested that tumor targeting with antibodies would result in a higher concentration of the active agent in the tumor (Deguchi, T. et al. (1986) *Cancer Res* 46: 3751-3755); however, this has not correlated in the treatment of human disease, likely because human tumors are much more heterogeneous in permeability than mouse tumors. Jain, R. K. et al. (2010) *Nat Rev Clin Oncol* 7:653-664. Also, the size of the nanoparticle is critical for extravasation from the vasculature into the tumor. In a mouse study using a human colon adenocarcinoma xenotransplant model, the vascular pores were permeable to liposomes up to 400 nm. Yuan, F., et al. (1995) *Cancer Res* 55: 3752-3756. Another study of tumor pore size and permeability demonstrated that both characteristics were dependent on tumor location and growth status, with regressing tumors and cranial tumors permeable to particles less than 200 nm. Hobbs, S. K., et al. (1998) *Proc Natl Acad Sci USA* 95:4607-4612. The nano-immune conjugate described herein overcomes this issue by the fact that the large complex, which is less than 200 nm intact, is partially dissociated in systemic circulation into smaller functional units that are easily able to permeate tumor tissue. Furthermore, once the conjugate arrives to the tumor site, the smaller toxic payload can be released and only the toxic portion needs to be taken up by tumor cells, not the entire conjugate.

The advent of antibody-(i.e. AVASTIN®) coated albumin nanoparticles containing a therapeutic agent (i.e., ABRAXANE®) has led to a new paradigm of directional delivery of two or more therapeutic agents to a predetermined site in vivo. See PCT Patent Publication Nos. WO 2012/154861 and WO 2014/055415, each of which is incorporated herein by reference in its entirety.

However, it is contemplated that some cancers will not be treated by the paclitaxel in the ABRAXANE®-antibody complexes, and/or that other therapeutic agents (e.g., anti-cancer chemotherapeutic agents) will be more effective in treating certain cancers. Herein are disclosed reduced toxicity nanoparticles (RTP) comprising a carrier protein (e.g., albumin) and a reduced amount of paclitaxel (e.g., compared to ABRAXANE®), or non-toxic nanoparticles (NTP) comprising a carrier protein (e.g., albumin) and a paclitaxel derivative that is less toxic than paclitaxel. The nanoparticles may further include a therapeutic agent and/or binding agents (e.g., antibodies).

Nanoparticles and Nanoparticle Compositions

As will be apparent to the skilled artisan upon reading this disclosure, the present disclosure relates to nanoparticles and compositions of nanoparticles containing a carrier protein (e.g., albumin) and a paclitaxel derivative (e.g., a derivative that is less toxic than paclitaxel) or a reduced amount of paclitaxel (e.g., compared to a therapeutic amount, and/or compared to an amount in ABRAXANE®). In some embodiments, the nanoparticles also contain binding agents and/or a therapeutic agent. In some embodiments, the nanoparticles or nanoparticle composition is lyophilized.

The present invention is further predicated, in part, on the formation of nanoparticles comprising a carrier protein and paclitaxel in a lower amount than is present in ABRAX- ANE® or a paclitaxel derivative that is less toxic (e.g., to cells) than paclitaxel, optionally with a binding agent and/or a therapeutic agent. Without being bound by theory, it is believed that such nanoparticles provide targeted therapy to a tumor while minimizing toxicity to the patient, and can be used to treat tumors that traditionally are not susceptible to paclitaxel and/or that respond better to a different therapeutic agent.

In some embodiments, the carrier protein can be albumin, gelatin, elastin (including topoelastin) or elastin-derived polypeptides (e.g., α-elastin and elastin-like polypeptides (ELPs)), gliadin, legumin, zein, soy protein (e.g., soy protein isolate (SPI)), milk protein (e.g., β-lactoglobulin (BLG) and casein), or whey protein (e.g., whey protein concentrates (WPC) and whey protein isolates (WPI)). In preferred embodiments, the carrier protein is albumin. In preferred embodiments, the albumin is egg white (ovalbumin), bovine serum albumin (BSA), or the like. In even more preferred embodiments, the carrier protein is human serum albumin (HSA). In some embodiments, the carrier protein is a recombinant protein (e.g., recombinant HSA). In some embodiments, the carrier protein is a generally regarded as safe (GRAS) excipient approved by the United States Food and Drug Administration (FDA).

In some embodiments, the binding agents are antibodies selected from ado-trastuzumab emtansine, alemtuzumab, atezolizumab, bevacizumab, cetuximab, denosumab, dinutuximab, ipilimumab, nivolumab, obinutuzumab, ofatumumab, panitumumab, pembrolizumab, pertuzumab, rituximab, avelumab or durvalumab, pidilizumab, BMS 936559, and trastuzumab. In some embodiments, the antibodies are selected from the antibodies listed in Table 1. In some embodiments, the antibodies are a substantially single layer of antibodies on all or part of the surface of the nanoparticle.

Table 1 depicts a list of non-limiting list of antibodies.

TABLE 1

| Antibodies | |
|---|---|
| Biologic | Treatment(s)/Target(s) |
| Rituximab (Rituxan ®) | Non-Hodgkin lymphoma |
| Alemtuzumab (Campath ®) | Chronic lymphocytic leukemia (CLL) |
| Ipilimumab (Yervoy ®) | Metastatic melanoma |
| Bevacizumab (Avastin ®) | Colon cancer, lung cancer, renal cancer, ovarian cancer, glioblastoma multiforme |
| Cetuximab (Erbitux ®) | Colorectal cancer, non-small cell lung cancer, head and neck cancer, cervical cancer, glioblastoma, ovarian epithelia, fallopian tube or primary peritoneal cancer, renal cell cancer |
| Panitumumab (Vectibix ®) | Colorectal cancer |
| Trastuzumab (Herceptin ®) | Breast cancer, Adenocarcinoma |
| $^{90}$Y-ibritumomab tiuxetan (Zevalin ®) | Non-Hodgkin lymphoma |
| Brentuximab vedotin (Adcetris ®) | Hodgkin lymphoma, Anaplastic large cell lymphoma |
| Blinatumomab (Blincyto) | Acute lymphocytic leukemia (ALL) |
| Pembrolizumab (Keytruda ®) | PD-1 (melanoma, non-small cell lung cancer) |
| Nivolumab (Opdivo ®) | PD-1 (melanoma, non-small cell lung cancer) |
| Ofatumumab (Arzerra ®) | Chronic lymphocytic leukemia (CLL) |
| Pertuzumab (Perjeta ®) | Breast cancer |
| Obinutuzumab (Gazyva ®) | Lymphoma, diffuse large B-cell lymphoma (DLBCL), indolent NHL (1st-line) |
| Din u tux imab (Unitux jn ®) | Neuroblastoma |
| Denosumab (Prolia ®) | Bone metastases, multiple myeloma, giant cell tumor of bone |
| RG6016 (LSD1 inhibitor) mAB Small molecule according to BioCentury BCIQ | Acute myelogenous leukemia (AML) |
| RG7882 (antibody drug conjugate) Alternative Names: D-4064A; DMUC 4064A; RG7882 | Pancreatic cancer, ovarian cancer |
| Lifastuzumab vedotin (antibody drug conjugate) | Platinum-resistant ovarian cancer, NSCLC |
| Polatuzumab vedotin (antibody drug conjugate) | DLBCL, NHL |
| RG7446 (anti-PD-L1 mAb) | bladder cancer, NSCLC, melanoma, breast, renal cell carcinoma, lymphoma |
| Atezolizumab (Tecentriq ®, anti-PD-L1) | Bladder cancer, metastatic NSCLC |
| DLYE-5953A (anti-Ly6E mAB cytotoxic drug conjugate) | Refractory solid tumors |
| Duligotuzumab(anti-HER3/EGFR DAF mAb) | Solid tumors with mutant KRAS |
| RG7117 (ERBB-3 receptor antagonist) | Metastatic breast cancer |
| RG7155 (CSF-1R antagonist) | Solid tumors |
| RG7450 (anti-STEAP1 antibody drug conjugate) | Prostate cancer |
| RG7802 (CD3/CEA bispecific antibody) | Solid tumors |
| RG7813 (CEA inhibitor) | Solid tumors |

TABLE 1-continued

Antibodies

| Biologic | Treatment(s)/Target(s) |
|---|---|
| RG7841 (antibody drug conjugate) | Solid tumors |
| RG7876 (CD40 antigen stimulant) | Solid tumors |
| RG7888 (anti-OX40 mAb) | Solid tumors |
| RG7221 (Ang2-VEGF mAb) | Metastatic colorectal cancer |
| RG7686 (glypican-3 mAb) | Hepatocellular carcinoma |
| Perjeta ® pertuzumab | HER3-positive breast cancer, gastric cancer |
| Avelumab (anti-PD-L1 mAb) | Solid tumor, gastric cancer, Merkel cell carcinoma, non-small cell lung cancer |
| Durvalumab (anti-PD-L1 mAb) | NSCLC, head and neck, bladder, gastric, pancreatic, HCC and blood cancers |
| Pidilizumab/CT-011(anti-PD-1 mAb) | Lymphoma, myeloma |
| BMS 936559/MDX-1105 (anti-PD-L1 mAb) | melanoma, non-small cell lung cancer |

In some embodiments, the at least one therapeutic agent is selected from abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

Table 2 depicts a list of non-limiting list of cancer therapeutic agents. In one embodiment, the therapeutic agent is selected from the agents recited in Table 2.

TABLE 2

Cancer therapeutic agents
Cancer Drugs

| Drug | Target(s) |
|---|---|
| Abitrexate (Methotrexate) | Acute lymphoblastic leukemia; breast cancer; gestational trophoblastic disease, head and neck cancer; lung cancer; mycosis fungoides; non-Hodgkin lymphoma; osteosarcoma |
| Ado-Trastuzumab Emtansine | Breast cancer |
| Adriamycin (Doxorubicin Hydrochloride) | Acute lymphoblastic leukemia; acute myeloid leukemia; breast cancer, gastric (stomach) cancer; Hodgkin lymphoma; neuroblastoma; non-Hodgkin lymphoma; ovarian cancer; small cell lung cancer; soft tissue and bone sarcomas; thyroid cancer; transitional cell bladder cancer; Wilms tumor |
| Adrucil, Efudex, Fluoroplex (Fluorouracil) | Basal cell carcinoma; breast cancer; colorectal cancer; gastric (stomach) adenocarcinoma; pancreatic cancer; squamous cell carcinoma of the head and neck |
| Afinitor (Everolimus) | Breast cancer, pancreatic cancer; renal cell carcinoma; subependymal giant cell astrocytoma |
| Alimta (Pemetrexed Disodium) | Malignant pleural mesothelioma; non-small cell lung cancer |
| Ambochlorin, Leukeran, or Linfolizin (Chlorambucil) | Chronic lymphocytic leukemia; Hodgkin lymphoma; non-Hodgkin lymphoma |
| Aredia (Pamidronate Disodium) | Breast cancer; multiple myeloma |
| Arimidex (Anastrozole) | Breast cancer |
| Aromasin (Exemestane) | Advanced breast cancer; early-stage breast cancer and estrogen receptor positive |
| Arranon (Nelarabine) | T-cell acute lymphoblastic leukemia; T-cell lymphoblastic lymphoma |
| BEACOPP | Hodgkin lymphoma |
| Becenum, BiCNU (Carmustine) | Brain tumors; Hodgkin lymphoma; multiple myeloma; non-Hodgkin lymphoma |
| Beleodaq (Belinostat) | Peripheral T-cell lymphoma |
| BEP | Ovarian germ cell tumors; testicular germ cell tumors |
| Bleomycin | Hodgkin lymphoma; non-Hodgkin lymphoma; penile cancer; squamous cell carcinoma of the cervix; squamous cell carcinoma of the head and neck; squamous cell carcinoma of the vulva; testicular cancer |

TABLE 2-continued

Cancer therapeutic agents
Cancer Drugs

| Drug | Target(s) |
| --- | --- |
| Bosulif (Bosutinib) | Chronic myelogenous leukemia |
| Busulfex or Myleran (Busulfan) | Chronic myelogenous leukemia |
| CAF | Breast cancer |
| Camptosar (Irinotecan Hydrochloride) | Colorectal cancer |
| CAPOX | Colorectal cancer |
| Casodex (Bicalutamide) | Prostate cancer |
| CeeNU (Lomustine) | Brain tumors; Hodgkin lymphoma |
| Ceritinib | Non-small cell lung cancer |
| CHOP | Non-Hodgkin lymphoma |
| Clofarex (Clofarabine) | Acute lymphoblastic leukemia |
| CMF | Breast cancer |
| Cometriq (Cabozantinib-S-Malate) | Medullary thyroid cancer |
| COPP | Hodgkin lymphoma; non-Hodgkin lymphoma |
| COPP-ABV | Hodgkin lymphoma |
| Cosmegen (Dactinomycin) | Ewing sarcoma; gestational trophoblastic disease; rhabdomyosarcoma; solid tumors; testicular cancer; Wilms tumor |
| CVP | Non-Hodgkin lymphoma; chronic lymphocytic leukemia |
| Cyfos (Ifosfamide) | Testicular germ cell tumors |
| Cytoxan or Neosar (Cyclophosphamide) | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non-Hodgkin lymphoma; ovarian cancer; retinoblastoma |
| Dacarbazine | Hodgkin lymphoma; melanoma |
| Dacogen (Decitabine) | Myelodysplastic syndromes |
| Degarelix | Prostate cancer |
| Denileukin Diftitox | Cutaneous T-cell lymphoma |
| Denosumab | Giant cell tumor of the bone; breast cancer, prostate cancer |
| DepoCyt ar DepoFoam (Liposomal Cytarabine) | Lymphomatous meningitis |
| DTIC-Dome (Dacarbazine) | Hodgkin lymphoma; melanoma |
| Ellence (Epirubicin Hydrochloride) | Breast cancer |
| Eloxatin (Oxaliplatin) | Colorectal cancer; stage III colon cancer |
| Emend (Aprepitant) | Nausea and vomiting caused by chemotherapy and nausea and vomiting after surgery |
| EPOCH | Non-Hodgkin lymphoma |
| Erbitux (Cetuximab) | Colorectal cancer; squamous cell carcinoma of the head and neck |
| Eribulin Mesylate | Breast cancer |
| Erivedge (Vismodegib) | Basal cell carcinoma |
| Erlotinib Hydrochloride | Non-small cell lung cancer; pancreatic cancer |
| Erwinaze (Asparaginase *Erwinia chrysanthemi*) | Acute lymphoblastic leukemia |
| Etopophos (Etoposide Phosphate) | Small cell lung cancer; testicular cancer |
| Evacet or LipoDox or Doxil (Doxorubicin Hydrochloride Liposome) | AIDS-related Kaposi sarcoma; multiple myeloma; ovarian cancer |
| Evista or Keoxifene (Raloxifene Hydrochloride) | Breast cancer |
| Fareston (Toremifene) | Breast cancer |
| Farydak (Panobinostat) | Multiple myeloma |
| Faslodex (Fulvestrant) | Breast cancer |
| FEC | Breast cancer |
| Femara (Letrozole) | Breast cancer |
| Filgrastim | Neutropenia |
| Fludara (Fludarabine Phosphate) | Chronic lymphocytic leukemia |
| FOLFIRI | Colorectal cancer |
| FOLFIRI-BEVACIZUMAB | Colorectal cancer |
| FOLFIRI-CETUXIMAB | Colorectal cancer |
| FOLFIRINOX | Pancreatic cancer |
| FOLFOX | Colorectal cancer |
| Folotyn (Pralatrexate) | Peripheral T-cell lymphoma |
| FU-LV | Colorectal cancer; esophageal cancer; gastric cancer |
| GEMCITABINE-CISPLATIN | Biliary tract cancer; bladder cancer; cervical cancer; malignant mesothelioma; non-small cell lung cancer; ovarian cancer; pancreatic cancer |
| GEMCITABINE-OXALIPLATIN | Pancreatic cancer |
| Gemzar (Gemcitabine Hydrochloride) | Breast cancer; non-small cell lung cancer; ovarian cancer; pancreatic cancer |

TABLE 2-continued

Cancer therapeutic agents
Cancer Drugs

| Drug | Target(s) |
| --- | --- |
| Gilotrif (Afatinib Dimaleate) | Non-small cell lung cancer |
| Gleevec (Imatinib Mesylate) | Acute lymphoblastic leukemia; chronic eosinophilic leukemia or hypereosinophilic syndrome; chronic myelogenous leukemia; dermatofibrosarcoma protuberans; gastrointestinal stromal tumor; myelodysplastic/myeloproliferative neoplasms; systemic mastocytosis. |
| Gliadel (Carmustine Implant) | Glioblastoma multiforme; malignant glioma |
| Halaven (Eribulin Mesylate) | Breast cancer |
| Hycamtin (Topotecan Hydrochloride) | Cervical cancer; ovarian cancer; small cell lung cancer |
| Hyper-CVAD | Acute lymphoblastic leukemia; non-Hodgkin lymphoma |
| Ibrance (Palbociclib) | Breast cancer |
| ICE | Hodgkin lymphoma; non-Hodgkin lymphoma |
| Iclusig (Ponatinib Hydrochloride) | Acute lymphoblastic leukemia; Chronic myelogenous leukemia |
| Idamycin (Idarubicin Hydrochloride) | Acute myeloid leukemia |
| Imbruvica (Ibrutinib) | Chronic lymphocytic leukemia; mantle cell lymphoma; Waldenström macroglobulinemia |
| Inlyta (Axitinib) | Renal cell carcinoma |
| Iressa (Gefitinib) | Non-small cell lung cancer |
| Istodax (Romidepsin) | Cutaneous T-cell lymphoma |
| Ixempra (Ixabepilone) | Breast cancer |
| Jevtana (Cabazitaxel) | Prostate cancer |
| Kyprolis (Carfilzomib) | Multiple myeloma |
| Lenvima (Lenvatinib Mesylate) | Thyroid cancer |
| Leuprolide Acetate | Prostate cancer |
| Lupron (Leuprolide Acetate) | Prostate cancer |
| Lynparza (Olaparib) | Ovarian cancer |
| Marqibo (Vincristine Sulfate Liposome) | Acute lymphoblastic leukemia |
| Matulane (Procarbazine Hydrochloride) | Hodgkin lymphoma |
| Megace (Megestrol Acetate) | Breast cancer; endometrial cancer |
| Mekinist (Trametinib) | Melanoma |
| Mesnex (Mesna) | Hemorrhagic cystitis |
| Mitoxantrone Hydrochloride | Acute myeloid leukemia; prostate cancer |
| Mitozytrex (Mitomycin C) | Gastric (stomach) and pancreatic adenocarcinoma |
| MOPP | Hodgkin lymphoma |
| Mozobil (Plerixafor) | Multiple myeloma; non-Hodgkin lymphoma |
| Mustargen (Mechlorethamine Hydrochloride) | Bronchogenic carcinoma; chronic lymphocytic leukemia; chronic myelogenous leukemia; Hodgkin lymphoma; malignant pleural effusion, malignant pericardial effusion, and malignant peritoneal effusion; mycosis fungoides; non-Hodgkin lymphoma |
| Mylotarg (Gemtuzumab Ozogamicin) | Acute myeloid leukemia |
| Navelbine (Vinorelbine Tartrate) | Non-small cell lung cancer |
| Nexavar (Sorafenib Tosylate) | Hepatocellular carcinoma; Renal cell carcinoma; Thyroid cancer |
| Nilotinib | Chronic myelogenous leukemia |
| Nolvadex (Tamoxifen Citrate) | Breast cancer |
| Odomzo (Sonidegib) | Basal cell carcinoma |
| OEPA | Hodgkin lymphoma |
| OFF | Pancreatic cancer |
| Oncaspar (Pegaspargase) | Acute lymphoblastic leukemia |
| OPPA | Hodgkin lymphoma |
| Paclitaxel | AIDS-related Kaposi sarcoma; Breast cancer; Non-small cell lung cancer; Ovarian cancer |
| PAD | Multiple myeloma |
| Paraplat (Carboplatin) | Non-small cell lung cancer; Ovarian cancer |
| Paraplatin (Carboplatin) | Non-small cell lung cancer; Ovarian cancer |
| Platinol (Cisplatin) | Bladder cancer; Cervical cancer; Malignant mesothelioma; Non-small cell lung cancer; Ovarian cancer; Squamous cell carcinoma of the head and neck; Testicular cancer |
| Pomalyst (Pomalidomide) | Multiple myeloma |
| Pontinib Hydrochloride | Acute lymphoblastic leukemia; Chronic myelogenous leukemia |
| Prednisone | Acute lymphoblastic leukemia; Chronic lymphocytic leukemia; Hodgkin lymphoma; Multiple myeloma; Non-Hodgkin lymphoma; Prostate cancer; Thymoma and thymic carcinoma |

TABLE 2-continued

Cancer therapeutic agents
Cancer Drugs

| Drug | Target(s) |
| --- | --- |
| Provenge (Sipuleucel-T) | Prostate cancer |
| Purinethol (Mercaptopurine) | Acute lymphoblastic leukemia |
| Radium 223 Dichloride | Prostate cancer |
| R-CHOP | Non-Hodgkin lymphoma |
| R-CVP | Non-Hodgkin lymphoma |
| R-EPOCH | B-cell non-Hodgkin lymphoma |
| Revlimid (Lenalidomide) | Mantle cell lymphoma; Multiple myeloma; Anemia |
| Rubidomycin (Daunorubicin Hydrochloride) | Acute lymphoblastic leukemia; Acute myeloid leukemia |
| Sipuleucel-T | Prostate cancer |
| Somatuline Depot (Lanreotide Acetate) | Gastroenteropancreatic neuroendocrine tumors |
| Sprycel (Dasatinib) | Acute lymphoblastic leukemia; Chronic myelogenous leukemia |
| STANFORD V | Hodgkin lymphoma |
| Stivarga (Regorafenib) | Colorectal cancer; Gastrointestinal stromal tumor |
| Sutent (Sunitinib Malate) | Gastronintestinal stromal tumor; Pancreatic cancer; Renal cell carcinoma |
| Synovir (Thalidomide) | Multiple myeloma |
| Synribo (Omacetaxine Mepesuccinate) | Chronic myelogenous leukemia |
| TAC | Breast cancer |
| Tafinlar (Dabrafenib) | Melanoma |
| Tarabine PFS (Cytarabine) | Acute lymphoblastic leukemia; Acute myeloid leukemia; Chronic myelogenous leukemia; meningeal leukemia |
| Tarceva (Erlotinib Hydrochloride) | Non-small cell lung cancer; Pancreatic cancer |
| Targretin (Bexarotene) | Skin problems caused by cutaneous T-cell lymphoma |
| Tasigna (Niltinib) | Chronic myelogenous leukemia |
| Taxol (Paclitaxel) | AIDS-related Kaposi sarcoma; Breast cancer; Non-small cell lung cancer; Ovarian cancer |
| Taxotere (Docetaxel) | Breast cancer; Adenocarcinoma; Non-small cell lung cancer; Prostate cancer; Squamous cell carcinoma of the head and neck; adenocarcinoma of the stomach or gastroesophageal junction; |
| Temodar or Methazolastone (Temozolomide) | Anaplastic astrocytoma; Glioblastoma multiforme |
| Thiotepa | Bladder cancer; Breast cancer; Malignant pleural effusion, malignant pericardial effusion, and malignant peritoneal effusion; Ovarian cancer |
| Toposar or VePesid (Etoposide) | Small cell lung cancer; Testicular cancer |
| Torisel (Temsirolimus) | Renal cell carcinoma |
| TPF | Squamous cell carcinoma of the head and neck; Gastric (stomach) cancer |
| Treanda (Bendamustine Hydrochloride) | B-cell non-Hodgkin lymphoma; Chronic lymphocytic leukemia |
| Trisenox (Arsenic Trioxide) | Acute promyelocytic leukemia |
| Tykerb (Lapatinib Ditosylate) | Breast cancer |
| Vandetabib | Medullary thyroid cancer |
| VAMP | Hodgkin lymphoma |
| VeIP | Ovarian germ cell; Testicular cancer |
| Velcade (Bortezomib) | Mulitple myeloma; Mantle cell lymphoma |
| Velsar or Velban (Vinblastine Sulfate) | Breast cancer; Choriocarcinoma; Hodgkin lymphoma; Kaposi sarcoma; Mycosis fungoides; Non-Hodgkin lymphoma; Testicular cancer |
| Viadur (Leuprolide Acetate) | Prostate cancer |
| Vidaza (Azacitidine) | Myelodysplastic syndromes |
| Vincasar PFS (Vincristine Sulfate) | Acute leukemia; Hodgkin lymphoma; Neuroblastoma; Non-Hodgkin lymphoma; Rhabdomyosarcoma; Wilms tumor |
| VIP | Testicular cancer |
| Visbodegib | Basal cell carcinoma |
| Votrient (Pazopanib Hydrochloride) | Renal cell carcinoma; Soft tissue sarcoma |
| Wellcovorin (Leucovorin Calcium) | Colorectal cancer; Anemia |
| Xalkori (Crizotinib) | Non-small cell lung cancer |
| Xeloda (Capecitabine) | Breast cancer; Colorectal cancer |
| XELIRI | Colorectal cancer; Esophageal cancer; Gastric (stomach) cancer |
| XELOX | Colorectal cancer |
| Xofigo (Radium 223 Dichloride) | Prostate cancer |
| Xtandi (Enzalutamide) | Prostate cancer |

TABLE 2-continued

Cancer therapeutic agents
Cancer Drugs

| Drug | Target(s) |
| --- | --- |
| Zaltrap (Ziv-Aflibercept) | Colorectal cancer |
| Zelboraf (Vemurafenib) | Melanoma |
| Zoladex (Goserelin Acetate) | Breast cancer; Prostate cancer |
| Zolinza (Vorinostat) | Cutaneous T-cell lymphoma |
| Zometa (Zoledronic Acid) | Multiple myeloma |
| Zydelig (Idelalisib) | Chronic lymphocytic leukemia; Non-Hodgkin lymphoma (Follicula B-cell non Hodgkin lymphoma and Small lymphocytic lymphoma) |
| Zykadia (Certinib) | Non-small cell lung cancer |
| Zytiga (Abiraterone Acetate) | Prostate cancer |

It is to be understood that the therapeutic agent may be located inside the nanoparticle, on the outside surface of the nanoparticle, or both. The nanoparticle may contain more than one therapeutic agent, for example, two therapeutic agents, three therapeutic agents, four therapeutic agents, five therapeutic agents, or more. Furthermore, a nanoparticle may contain the same or different therapeutic agents inside and outside the nanoparticle.

In one aspect, the nanoparticle comprises at least 100 binding agents non-covalently bound to the surface of the nanoparticle. In one aspect, the nanoparticle comprises at least 200, 300, 400, 500, 600, 700 or 800 binding agents non-covalently bound to the surface of the nanoparticle.

In one aspect, the nanoparticle comprises between about 100 and about 1000 binding agents non-covalently bound to the surface of the nanoparticle. In one aspect, the nanoparticle comprises between about 200 and about 1000, between about 300 and about 1000, between about 400 and about 1000, between about 500 and about 1000, between about 600 and about 1000, between about 200 and about 800, between about 300 and about 800, or between about 400 and about 800 binding agents non-covalently bound to the surface of the nanoparticle. Contemplated values include any value or subrange within any of the recited ranges, including endpoints.

In one aspect, the average particle size in the nanoparticle composition is less than about 1 µm. In one aspect, the average particle size in the nanoparticle composition is between about 50 nm and about 1 µm. In one aspect, the average particle size in the nanoparticle composition is between about 60 nm and about 900 nm. In one aspect, the average particle size in the nanoparticle composition is between about 60 nm and about 800 nm. In one aspect, the average particle size in the nanoparticle composition is between about 60 nm and about 700 nm. In one aspect, the average particle size in the nanoparticle composition is between about 60 nm and about 600 nm. In one aspect, the average particle size in the nanoparticle composition is between about 60 nm and about 500 nm. In one aspect, the average particle size in the nanoparticle composition is between about 60 nm and about 400 nm. In one aspect, the average particle size in the nanoparticle composition is between about 60 nm and about 300 nm. In one aspect, the average particle size in the nanoparticle composition is between about 60 nm and about 200 nm. In one aspect, the average particle size in the nanoparticle composition is between about 80 nm and about 900 nm, 800 nm, 700 nm, 600 nm, 500 nm, 400 nm, 300 nm, or 200 nm. In one aspect, the average particle size in the nanoparticle composition is between about 100 nm and about 900 nm, 800 nm, 700 nm, 600 nm, 500 nm, 400 nm, 300 nm, or 200 nm. In one aspect, the average particle size in the nanoparticle composition is between about 120 nm and about 900 nm, 800 nm, 700 nm, 600 nm, 500 nm, 400 nm, 300 nm, or 200 nm. Contemplated values include any value, subrange, or range within any of the recited ranges, including endpoints.

In one aspect, the nanoparticle composition is formulated for intravenous injection. In order to avoid an ischemic event, the nanoparticle composition formulated for intravenous injection should comprise nanoparticles with an average particle size of less than about 1 µm.

In one aspect, the average particle size in the nanoparticle composition is greater than about 1 µm. In one aspect, the average particle size in the nanoparticle composition is between about 1 µm and about 5 µm, between about 1 µm and about 4 µm, between about 1 µm and about 3 µm, between about 1 µm and about 2 µm, or between about 1 µm and about 1.5 µm. Contemplated values include any value, subrange, or range within any of the recited ranges, including endpoints.

In one aspect, the nanoparticle composition is formulated for direct injection into a tumor. Direct injection includes injection into or proximal to a tumor site, perfusion into a tumor, and the like. When formulated for direct injection into a tumor, the nanoparticle may comprise any average particle size. Without being bound by theory, it is believed that larger particles (e.g., greater than 500 nm, greater than 1 µm, and the like) are more likely to be immobilized within the tumor, thereby providing a beneficial effect. Larger particles can accumulate in the tumor or specific organs. See, e.g., 20-60 micron glass particle that is used to inject into the hepatic artery feeding a tumor of the liver, called "THERA-SPHERE®" (in clinical use for liver cancer). Therefore, for intravenous administration, particles under 1 µm are typically used. Particles over 1 µm are, more typically, administered directly into a tumor ("direct injection") or into an artery feeding into the site of the tumor.

In one aspect, less than about 0.01% of the nanoparticles within the composition have a particle size greater than 200 nm, greater than 300 nm, greater than 400 nm, greater than 500 nm, greater than 600 nm, greater than 700 nm, or greater than 800 nm. In one aspect, less than about 0.001% of the nanoparticles within the composition have a particle size greater than 200 nm, greater than 300 nm, greater than 400 nm, greater than 500 nm, greater than 600 nm, greater than 700 nm, or greater than 800 nm. In a preferred embodiment, less than about 0.01% of the nanoparticles within the composition have a particle size greater than 800 nm. In a more preferred embodiment, less than about 0.001% of the nanoparticles within the composition have a particle size greater than 800 nm.

In a preferred aspect, the sizes and size ranges recited herein relate to particle sizes of the reconstituted lyophilized nanoparticle composition. That is, after the lyophilized nanoparticles are resuspended in an aqueous solution (e.g., water, other pharmaceutically acceptable excipient, buffer, etc.), the particle size or average particle size is within the range recited herein.

In one aspect, at least about 50%, 60%, 70%, 80%, 90%, 95%, 96%, 97%, 98%, 99%, 99.5%, or 99.9% of the nanoparticles are present in the reconstituted composition as single nanoparticles. That is, fewer than about 50%, 40%, 30%, etc. of the nanoparticles are dimerized or multimerized (oligomerized).

In some embodiments, the nanoparticles in the composition have less than 20% by number dimerization, less than 10% by number dimerization and preferably less than 5% dimerization.

In some embodiments, the size of the nanoparticle can be controlled by the adjusting the amount (e.g., ratio) of carrier protein to paclitaxel or paclitaxel derivative, and/or ratio of carrier protein-paclitaxel (or paclitaxel derivative) nanoparticles to binding agent. The size of the nanoparticles, and the size distribution, is also important. The nanoparticles of the invention may behave differently according to their size. At large sizes, an agglomeration may block blood vessels. Therefore, agglomeration of nanoparticles can affect the performance and safety of the composition. On the other hand, larger particles may be more therapeutic under certain conditions (e.g., when not administered intravenously).

Further challenges are imposed because the nanoparticles are used in therapy.

While rearrangement of the components in the nanoparticle may be mitigated through covalent bonds between the components, such covalent bonds pose challenges for the therapeutic use of nanoparticles in cancer treatment. The binding agent, carrier protein, and therapeutic agent typically act at different locations in a tumor and through different mechanisms. Non-covalent bonds permit the components of the nanoparticle to dissociate at the tumor. Thus, while a covalent bond may be advantageous for lyophilization, it may be disadvantageous for therapeutic use.

The size of nanoparticles, and the distribution of the size, is also important. Nanoparticles may behave differently according to their size. At large sizes, nanoparticles or the agglomeration of the particles may block blood vessels either of which can affect the performance and safety of the composition.

Paclitaxel Derivatives

Paclitaxel derivatives used in the present invention preferably are less toxic than paclitaxel. That is, the paclitaxel derivative is less toxic to cells (e.g., does not kill cancer and/or normal cells as well as, or does not inhibit cell proliferation as well as) compared to paclitaxel. Paclitaxel derivatives may include any derivative or precursor of paclitaxel. Examples include, but are not limited to, 20-Acetoxy-4-deactyl-5-epi-20, O-secotaxol (the Meerwein Product of Paclitaxel), or Baccatin III ((2β,5α,7α,10α,13β)-4,10-Diacetoxy-1,7,13-trihydroxy-9-oxo-5,20-epoxytax-11-en-2-yl benzoate).

For example, most of the C-13 simplified paclitaxel derivatives and derivatives of different stereochemistry demonstrated reduced activity in comparison to paclitaxel. The 2'-hydroxyl and the 3'-benzamido group are not essential for bioactivity, but are important for strong microtubule binding and cytotoxicity. Formation of ethers at 2'-hydroxyl group, such as alkyl ether (e.g., methyl ether) and alkyl silyl ether (e.g., ter-butyldimethylsilyl ether), reduced cytotoxicity. Acylation of the 2'-hydroxyl group (e.g., 2'-acetyltaxol) also leads to loss of activity. Replacement of 2'-hydroxyl group by halogen (e.g, fluorine) was also found to significantly reduce the cytotoxicity. Lead tetracetate oxidation of 6α-hydroxy-7-epi-paclitaxel leads to C-nor-paclitaxel and C-seco-paclitaxel derivatives. Tetrapropylammonium perruthenate (TPAP) oxidation of a 6α-hydroxy-7-epi-paclitaxel derivative leads to a 6-formyl-C-nor-paclitaxel derivative. Reaction of a 6α-O-trifluoromethanesulfonyl-7-epi-paclitaxel derivative with DMAP yields a 20-O-acetyl-4-deacetyl-5,6-dehydro-6-formyl-C-nor-paclitaxel derivative. C-nor-paclitaxel analogs are less active than paclitaxel. Therefore, the paclitaxel derivative may include modifications at any one or more of these sites or produced by one or more of these methods. See, e.g., Liang et al. *Tetrahedron*, 53(10):3441-3456 (1997); U.S. Pat. Nos. 5,756,301; 5,981,777; each of which is incorporated by reference herein in its entirety.

Methods of Making Nanoparticles and Nanoparticle Complexes

In some aspects, the current invention relates to methods of making nanoparticle compositions as described herein. In some embodiments, this disclosure relates to methods of making the nanoparticle compositions, wherein said method comprises contacting the carrier protein and the paclitaxel or paclitaxel derivative under conditions and ratios of components that will allow for formation of the desired nanoparticles. In some embodiments, the methods further relate to contacting a nanoparticle with binding agents and/or therapeutic agent under conditions to form nanoparticle complexes.

In some embodiments, the nanoparticles are made by combining the carrier protein and paclitaxel or paclitaxel derivative, and homogenizing under high pressure to form stable nanoparticles. Non-limiting methods for homogenizing albumin and taxane (e.g., paclitaxel) can be found, for example, in Example 1, as well as U.S. Pat. Nos. 5,916,596; 6,506,405; and 6,537,579, each of which is incorporated herein by reference in its entirety.

In one embodiment, binding agents and/or therapeutic agents are complexed to the nanoparticles as described, for example, in U.S. Pat. Nos. 9,757,453; and 9,446,148.

In some aspects, provided herein are methods of making nanoparticle complexes, wherein said methods comprise contacting the carrier protein-paclitaxel (or paclitaxel derivative) nanoparticle with the binding agents and/or therapeutic agent in a solution having a pH of between 5.0 and 7.5 and a temperature between about 5° C. and about 60° C., between about 23° C. and about 60° C., or between about 55° C. and about 60° C. under conditions and ratios of components that will allow for formation of the desired nanoparticles. In one embodiment, the nanoparticle is made at 55-60° C. and pH 7.0. In another aspect, provided herein are methods of making the nanoparticle complexes, wherein said method comprises (a) homogenizing the carrier protein and paclitaxel (or paclitaxel derivative) to form a nanoparticle core; and (b) contacting the core with the antibodies in a solution having a pH of about 5.0 to about 7.5 at a temperature between about 5° C. and about 60° C., between about 23° C. and about 60° C., or between about 55° C. and about 60° C. under conditions and ratios of components that will allow for formation of the desired nanoparticle complexes.

Another embodiment of the invention includes a method for making a nanoparticle composition by facilitating complex formation of a protein carrier and a therapeutic agent, the method comprising contacting the carrier protein, an amount of paclitaxel as described herein, and a therapeutic agent in a solution having a pH of 5.0 or greater and a temperature between about 5° C. and about 60° C., to generate a nanoparticle. In yet another embodiment, the method further comprises contacting the protein-carrier complex with a binding agent.

The amount of components (e.g., carrier protein, antibodies, paclitaxel or paclitaxel derivative, therapeutic agents, combinations thereof) is controlled in order to provide for formation of the desired nanoparticles. A composition wherein the amount of components is too dilute will not form the nanoparticles as described herein. An overly concentrated solution will result in unstructured aggregates.

In a preferred embodiment, weight ratio of carrier protein to binding agent is 10:4. In some embodiments, the amount of carrier protein is between about 1 mg/mL and about 100 mg/mL. In some embodiments, the amount of binding agent is between about 1 mg/mL and about 30 mg/mL. For example, in some embodiments, the ratio of carrier protein: binding agent:solution is approximately 9 mg of carrier protein (e.g., albumin) to 4 mg of binding agent (e.g., BEV) in 1 mL of solution (e.g., saline).

In one embodiment, the amount of solution or other liquid medium employed to form the nanoparticles is particularly important. In some embodiments, the amount of solution (e.g., sterile water, saline, phosphate buffered saline) employed is between about 0.5 mL of solution to about 20 mL of solution.

In one aspect, the nanoparticle complexes of the nanoparticle composition are formed by contacting the carrier protein-paclitaxel (opr paclitaxel derivative) nanoparticles and at least one therapeutic agent with the binding agent at a ratio of about 10:1 to about 10:30 carrier protein particle or carrier protein-therapeutic agent particle to binding agent. In one embodiment, the ratio is about 10:2 to about 10:25. In one embodiment, the ratio is about 10:2 to about 1:1. In a preferred embodiment, the ratio is about 10:2 to about 10:6. In an especially preferred embodiment, the ratio is about 10:4. Contemplated ratios include any value, subrange, or range within any of the recited ranges, including endpoints.

In one aspect, the nanoparticles of the nanoparticle composition are formed by contacting the carrier protein-paclitaxel (or paclitaxel derivative) nanoparticles and at least one therapeutic agent. In one embodiment, the ratio is about 10:2 to about 10:25. In one embodiment, the ratio is about 10:2 to about 1:1. In a preferred embodiment, the ratio is about 10:2 to about 10:6. In an especially preferred embodiment, the ratio is about 10:4. Contemplated ratios include any value, subrange, or range within any of the recited ranges, including endpoints.

In one embodiment, the carrier protein-paclitaxel (or paclitaxel derivative) nanoparticles are contacted with the binding agent in a solution having a pH between about 4 and about 8. In one embodiment, the carrier protein-paclitaxel (or paclitaxel derivative) nanoparticles are contacted with the binding agent in a solution having a pH of about 4. In one embodiment, the carrier protein-paclitaxel (or paclitaxel derivative) nanoparticles are contacted with the binding agent in a solution having a pH of about 5. In one embodiment, the carrier protein-paclitaxel (or paclitaxel derivative) nanoparticles are contacted with the binding agent in a solution having a pH of about 6. In one embodiment, the carrier protein-paclitaxel (or paclitaxel derivative) nanoparticles are contacted with the binding agent in a solution having a pH of about 7. In one embodiment, the carrie carrier protein-paclitaxel (or paclitaxel derivative) nanoparticles are contacted with the binding agent in a solution having a pH of about 8. In a preferred embodiment, the carrier protein-paclitaxel (or paclitaxel derivative) nanoparticles are contacted with the binding agent in a solution having a pH between about 5 and about 7.

In one embodiment, the carrier protein-paclitaxel (or paclitaxel derivative) nanoparticles are incubated with the binding agent at a temperature of about 5° C. to about 60° C., or any range, subrange, or value within that range including endpoints. In a preferred embodiment, the carrier protein-paclitaxel (or paclitaxel derivative) nanoparticles are incubated with the binding agent at a temperature of about 23° C. to about 60° C.

Without being bound by theory, it is believed that the stability of the nanoparticle complexes is, at least in part, dependent upon the temperature and/or pH at which the nanoparticles are formed, as well as the concentration of the components (i.e., carrier protein, binding agent, paclitaxel or paclitaxel derivative, and a therapeutic agent) in the solution. In one embodiment, the $K_d$ of the nanoparticles is between about $1\times10^{-11}$ M and about $2\times10^{-5}$ M. In one embodiment, the $K_d$ of the nanoparticles is between about $1\times10^{-11}$ M and about $2\times10^{-8}$ M. In one embodiment, the $K_d$ of the nanoparticles is between about $1\times10^{-11}$ M and about $7\times10^{-9}$ M. In a preferred embodiment, the $K_d$ of the nanoparticles is between about $1\times10^{-11}$ M and about $3\times10^{-8}$ M. Contemplated values include any value, subrange, or range within any of the recited ranges, including endpoints.

Making Reduced-Toxicity Nanoparticles

The relative weight ratio of the carrier protein to the paclitaxel is greater than about 9:1. In one embodiment, the carrier protein and the paclitaxel have a relative weight ratios of greater than about 10:1, or about 11:1, or about 12:1, or about 13:1, or about 14:1, or about 15:1, or about 16:1, or about 17:1, or about 18:1, or about 19:1, or about 20:1, or about 21:1, or about 22:1, or about 23:1, or about 24:1, or about 25:1, or about 26:1, or about 27:1, or about 28:1, or about 29:1, or about 30:1. In one embodiment, the weight ratio is between 10:1 and 100:1, between 10:1 and 50:1, between 10:1 and 40:1, between 10:1 and 30:1, between 10:1 and 20:1, or between 10:1 and 15:1. In one embodiment, the weight ratio is between 15:1 and 50:1, 15:1 and 50:1, between 15:1 and 40:1, between 15:1 and 30:1, or between 15:1 and 20:1. The weight ratio may be any value or subrange within the recited ranges, including endpoints.

In one embodiment, the amount of paclitaxel is equal to a minimum amount capable of providing stability to the nanoparticles. In one embodiment, the amount of paclitaxel is greater than or equal to a minimum amount capable of providing affinity of the at least one therapeutic agent to the protein carrier. In one embodiment, the amount of paclitaxel is greater than or equal to a minimum amount capable of facilitating complex formation of the at least one therapeutic agent and the protein carrier. For example, less than about 1 mg of taxol can be added 9 mg of carrier protein (10 mg carrier protein-therapeutic) and 4 mg of binding agent, e.g., antibody, Fc fusion molecule, or aptamer, in 1 mL of solution.

It is to be noted that, when using a typical i.v. bag, for example, with the solution of approximately 1 liter one would need to use 1000× the amount of carrier protein/carrier protein-therapeutic agent and antibodies compared to that used in 1 mL. Thus, one cannot form the present nanoparticles in a standard i.v. bag. Furthermore, when the components are added to a standard i.v. bag in the therapeutic amounts of the present invention, the components do not self-assemble to form nanoparticles.

In one embodiment, the amount of paclitaxel present in the nanoparticle composition is less than about 5 mg/mL. In one embodiment, the amount of paclitaxel present in the nanoparticle composition is less than about 4.54 mg/mL, or about 4.16 mg/mL, or about 3.57 mg/mL, or about 3.33 mg/mL, or about 3.12 mg/mL, or about 2.94 mg/mL, or about 2.78 mg/mL, or about 2.63 mg/mL, or about 2.5 mg/mL, or about 2.38 mg/mL, or about 2.27 mg/mL, or about 2.17 mg/mL, or about 2.08 mg/mL, or about 2 mg/mL, or about 1.92 mg/mL, or about 1.85 mg/mL, or about 1.78 mg/mL, or about 1.72 mg/mL, or about 1.67 mg/mL. In one embodiment, the amount of paclitaxel present in the nanoparticle composition is greater than or equal to a minimum amount capable of providing stability to the nanoparticles. In one embodiment, the amount of paclitaxel present in the nanoparticle composition is greater than or equal to a minimum amount capable of providing affinity of the at least one therapeutic agent to the protein carrier. In one embodiment, the amount of paclitaxel present in the nanoparticle composition is greater than or equal to a minimum amount capable of facilitating complex formation of the at least one therapeutic agent and the protein carrier.

In one embodiment, the nanoparticle compositions described herein includes no binding agents.

Lyophilization

While protein compositions comprising a single source protein are commonly stored in lyophilized form where they exhibit significant shelf-life, such lyophilized compositions do not contain a self-assembled nanoparticle of two different proteins integrated together by hydrophobic-hydrophobic interactions. Moreover, the nanoparticle configuration wherein a majority of the binding portions of the binding agent are exposed on the surface of the nanoparticles lends itself to being susceptible to dislodgement or reconfiguration by conditions which otherwise would be considered benign. For example, during lyophilization, ionic charges on the proteins are dehydrated thereby exposing the underlying charges. Exposed charges allow for charge-charge interactions between the two proteins which can alter the binding affinity of each protein to the other. In addition, the concentration of the nanoparticles increases significantly as the solvent (e.g., water) is removed. Such increased concentrations of nanoparticles could lead to irreversible oligomerization. Oligomerization is a known property of proteins that reduces the biological properties of the oligomer as compared to the monomeric form and increases the size of the particle sometimes beyond 1 micron.

On the other hand, a stable form of a nanoparticle composition is required for clinical and/or commercial use where a shelf-life of at least 3 months is required and shelf-lives of greater than 6 months or 9 months are preferred. Such a stable composition must be readily available for intravenous injection, must retain its self-assembled form upon intravenous injection so as to direct the nanoparticle to the predetermined site in vivo, must have a maximum size of less than 1 micron so as to avoid any ischemic event when delivered into the blood stream, and finally must be compatible with the aqueous composition used for injection.

Lyophilization, or freeze-drying, removes water from a composition. In the process, the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al., Pharm. Res. 8(3):285-291 (1991).

While proteins may be lyophilized, the process of lyophilization and reconstitution may affect the properties of the protein. Because proteins are larger and more complex than traditional organic and inorganic drugs (i.e. possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland, et al., Critical Reviews in Therapeutic Drug Carrier Systems 10(4): 307-377 (1993).

Finally, cryoprotectants and agents that assist in the lyophilization process must be safe and tolerated for therapeutic use.

The lyophilized compositions of this invention are prepared by standard lyophilization techniques with or without the presence of stabilizers, buffers, etc. Surprisingly, these conditions do not alter the relatively fragile structure of the nanoparticles. Moreover, at best, these nanoparticles retain their size distribution upon lyophilization and, more importantly, can be reconstituted for in vivo administration (e.g., intravenous delivery) in substantially the same form and ratios as if freshly made.

In some embodiments, the nanoparticles (e.g., RTP or NTP) are lyophilized. In some embodiments, the nanoparticle complexes (e.g., RTP or NTP with associated therapeutic agent and/or binding agents) are lyophilized. In some embodiments, upon reconstitution with an aqueous solution, an amount of the binding agents are arranged on a surface of the nanoparticles. In some embodiments, the nanoparticle complexes are capable of binding to an antigen. In some embodiments, the antibodies associated with the nanoparticle complexes remain capable of binding to the antigen.

Formulations

In one aspect, the nanoparticle composition is formulated for systemic delivery, e.g., intravenous administration.

In one aspect, the nanoparticle composition is formulated for direct injection into a tumor. Direct injection includes injection into or proximal to a tumor site, perfusion into a tumor, and the like. Because the nanoparticle composition is not administered systemically, a nanoparticle composition is formulated for direct injection into a tumor may comprise any average particle size. Without being bound by theory, it is believed that larger particles (e.g., greater than 500 nm, greater than 1 µm, and the like) are more likely to be immobilized within the tumor, thereby providing what is believed to be a better beneficial effect.

In another aspect, provided herein is a composition comprising a compound provided herein, and at least one pharmaceutically acceptable excipient.

In general, the compounds provided herein can be formulated for administration to a patient by any of the accepted modes of administration. Various formulations and drug delivery systems are available in the art. See, e.g., Gennaro, A. R., ed. (1995) Remington's *Pharmaceutical Sciences*, 18th ed., Mack Publishing Co.

In general, compounds provided herein will be administered as pharmaceutical compositions by any one of the following routes: oral, systemic (e.g., transdermal, intranasal or by suppository), or parenteral (e.g., intramuscular, intravenous or subcutaneous) administration.

The compositions are comprised of, in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Treatment Methods

The nanoparticle compositions as described herein are useful in treating cancer cells and/or tumors in a mammal. In a preferred embodiment, the mammal is a human (i.e., a human patient). Preferably, a lyophilized nanoparticle composition is reconstituted (suspended in an aqueous excipient) prior to administration.

In one aspect is provided a method for treating a cancer cell, the method comprising contacting the cell with an effective amount of nanoparticle composition as described herein to treat the cancer cell. Treatment of a cancer cell includes, without limitation, reduction in proliferation, killing the cell, preventing metastasis of the cell, and the like.

In one aspect is provided a method for treating a tumor in a patient in need thereof, the method comprising administering to the patient a therapeutically effective amount of a nanoparticle composition as described herein to treat the tumor. In one embodiment, where the nanoparticles include a binding agent comprising an antigen-binding domain, the method comprises selecting a patient having a cancer which expresses the antigen. In one embodiment, the size of the tumor is reduced. In one embodiment, the tumor size does not increase (i.e. progress) for at least a period of time during and/or after treatment.

In one embodiment, the nanoparticle composition is administered intravenously. In one embodiment, the nanoparticle composition is administered directly to the tumor. In one embodiment, the nanoparticle composition is administered by direct injection or perfusion into the tumor.

In one embodiment, the method comprises:
a) administering the nanoparticle composition once a week for three weeks;
b) ceasing administration of the nanoparticle composition for one week; and
c) optionally repeating steps a) and b) as necessary to treat the tumor.

In one embodiment, the therapeutically effective amount of the nanoparticles described herein comprises about 1 $mg/m^2$ to about 200 $mg/m^2$ antibody, about 2 $mg/m^2$ to about 150 $mg/m^2$, about 5 $mg/m^2$ to about 100 $mg/m^2$, about 10 $mg/m^2$ to about 85 $mg/m^2$, about 15 $mg/m^2$ to about 75 $mg/m^2$, about 20 $mg/m^2$ to about 65 $mg/m^2$, about 25 $mg/m^2$ to about 55 $mg/m^2$, about 30 $mg/m^2$ to about 45 $mg/m^2$, or about 35 $mg/m^2$ to about 40 $mg/m^2$ antibody. In other embodiments, the therapeutically effective amount comprises about 20 $mg/m^2$ to about 90 $mg/m^2$ antibody. In one embodiment, the therapeutically effective amount comprises 30 $mg/m^2$ to about 70 $mg/m^2$ antibody.

In one embodiment, the therapeutically effective amount of the nanoparticles described herein comprises about 50 $mg/m^2$ to about 200 $mg/m^2$ carrier protein or carrier protein and therapeutic agent. In one embodiment, the therapeutically effective amount of the nanoparticle compositions described herein comprise no binding agents. In one embodiment, the therapeutically effective amount of the nanoparticle compositions described herein comprise less than about a therapeutically effective amount of paclitaxel. In a preferred embodiment, the therapeutically effective amount comprises about less than 75 $mg/m^2$ of paclitaxel. Contemplated values include any value, subrange, or range within any of the recited ranges, including endpoints.

In one embodiment, the therapeutically effective amount comprises about 20 $mg/m^2$ to about 90 $mg/m^2$ binding agent, e.g., antibody, aptamer or fusion protein. In a preferred embodiment, the therapeutically effective amount comprises 30 $mg/m^2$ to about 70 $mg/m^2$ binding agent, e.g., antibody, aptamer or fusion protein. Contemplated values include any value, subrange, or range within any of the recited ranges, including endpoints.

Cancers or tumors that can be treated by the compositions and methods described herein include, but are not limited to the cancers referred to in the above tables, as well as: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors include breast cancer, lymphoma, multiple myeloma, and melanoma.

In general, the compounds of this invention will be administered in a therapeutically effective amount by any of the accepted modes of administration for agents that serve similar utilities. The actual amount of the compound of this invention, i.e., the nanoparticles, will depend upon numerous factors such as the severity of the disease to be treated, the age and relative health of the subject, the potency of the compound used, the route and form of administration, and other factors well known to the skilled artisan.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) *Remington's Pharmaceutical Sciences*, 18th ed., Mack Publishing Co.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

In related embodiments, the treatment comprises administration of the targeting binding agent prior to administration of the nanoparticles. In one embodiment, the targeting binding agent is administered between about 6 and 48, or 12 and 48 hours prior to administration of the nanoparticles. In another embodiment, the targeting binding agent is administered between 6 and 12 hours prior to administration of the nanoparticles. In yet another embodiment, the targeting binding agent is administered between 2 and 8 hours prior to administration of the nanoparticles. In still other embodiments, the targeting binding agent is administered a week prior to administration of the nanoparticles. For example, administration of a dose of BEV 24 hours prior to administration of nanoparticle complexes comprising bevacizumab or other VEGF-binding antibody. In another example, prior administration of rituximab prior to administering rituximab-containing nanoparticle complexes. The binding agent administered prior to the nanoparticle may be administered as a dose that is subtherapeutic, such as ½, ¹⁄₁₀th or ¹⁄₂₀ the amount normally considered therapeutic. Thus, in humans, pretreatment with BEV may comprise administration of 1 mg/kg BEV which is ¹⁄₁₀th the usual dose, followed by administration of the nanoparticles or nanoparticle complexes.

EXAMPLES

The present disclosure is illustrated using nanoparticles composed of albumin-bound paclitaxel or paclitaxel derivative as a core, and bevacizumab (i.e., Avastin®) or Rituximab (i.e., Rituxan®) as antibodies.

One skilled in the art would understand that making and using the nanoparticles of the Examples are for the sole purpose of illustration, and that the present disclosure is not limited by this illustration.

Any abbreviation used herein, has normal scientific meaning. All temperatures are ° C. unless otherwise stated. Herein, the following terms have the following meanings unless otherwise defined:

| | | |
|---|---|---|
| ABX | = | ABRAXANE ®/(albumin-bound paclitaxel |
| ADC | = | antibody dependent chemotherapy |
| BEV | = | bevacizumab |
| BSA | = | bovine serum albumin |
| nM | = | nanomolar |
| FITC | = | Fluorescein |
| Kd | = | dissociation constant |
| kg | = | kilogram |
| M | = | molar |
| mg | = | milligram |
| ml or mL | = | milliliter |
| $m^2$ | = | square meters |
| $mm^3$ | = | cubic millimeter |
| μg | = | microgram |
| μl | = | microliter |
| μm | = | micrometer/micron |
| PBS | = | Phosphate buffered saline |
| RT | = | room temperate |
| rpm | = | rotations per minute |

Example 1

Nanoparticle Preparation

Paclitaxel was reacted with Meerwein's Reagent breaking according to the reaction scheme laid out by Samaranayake et al. in "Modified Taxols. Reaction of Taxol with Electrophilic Reagents and Preperation of a Rearranged Taxol Derivative with Tubulin Assembly Activity" (*J. Org. Chem.* 1991, 56, 5114-5119), which is incorporated herein by reference in its entirety. This reaction breaks the C-4,C-5 oxetane ring severely inhibiting toxicity. The reaction and purification were performed by Organix Inc. (Woburn, Mass.). The reaction is shown in FIG. 1.

The Meerwein's Product of Paclitaxel (20-Acetoxy-4-deactyl-5-epi-20, O-secotaxol) was then homogenized under high pressure with albumin to form stable non-toxic nanoparticles (NTP). Methods for homogenizing albumin and taxane (e.g., paclitaxel) can be found, for example, in U.S.

Pat. Nos. 5,916,596; 6,506,405; and 6,537,579, each of which is incorporated herein by reference in its entirety.

Briefly, human serum albumin (HSA; Sigma Aldrich) was dissolved in sterile water at 1-1.5% w/v. In a separate container, 20-Acetoxy-4-deactyl-5-epi-20, O-secotaxol (10% w/w to HSA) was dissolved in chloroform to 10 mg/ml. Chloroform solution was added to the albumin solution and mixed with a hand-held homogenizer for 5 minutes at low RPM. The solution was run through micro-homogenizing pump at 20,000 PSI for 15 cycles. Pump coiled pathway and collection tube were placed in an ice bath to prevent solution from reaching dangerously high temps (i.e. over 50° C.). The solution was transferred to a rotary evaporator with a cold trap and run at reduced pressure for 45 minutes to evaporate off chloroform. The solution was filtered through 200 nm cellulose acetate filter.

For lyophilized nanoparticles, the solution was split into freeze drying flasks at appropriate volumes to allow full lyophilization of product. Flask with solution were placed at −80° C. for 2-4 hours. The frozen solution in the flasks were lyophilized using a bench top freeze dryer with condenser of −85° C. at <20 mtorr.

Example 2

Binding of NTP and Bevacizumab In Vitro

To determine whether NTP and bevacizumab (BEV) interact, the size of the NTP formed in Example 1 was analyzed by Malvern Nanosight technology, alone and after incubation with 4, 6, 8, and 10 milligrams per milliliter (mg/mL) of bevacizumab for 30 minutes.

Increasing nanoparticle diameter with increased concentration of BEV (FIGS. 2A-2E) suggests increased non-covalent coating of NTP with BEV. Diameter was measured at a 1:300 dilution using Malvern Nanosight technology.

Example 3

Affinity of Bevacizumab and Rituximab Binding to Non-Toxic Nanoparticles (NTP)

Figure 3A:
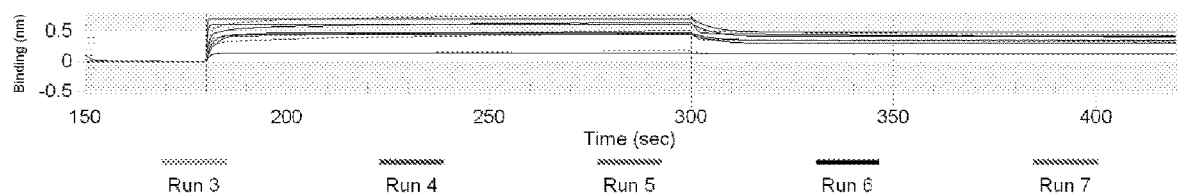
FIGS. 3A and 3B show the binding affinity (Kd) of bevacizumab (FIG. 3A) or rituximab (FIG. 3B) to NTP. Kd was measured using Bio Layer Interferometry Technology.
Figure 3B:
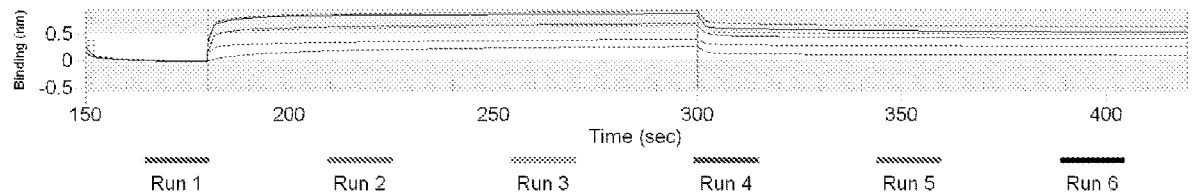

Binding affinity ($K_d$) of both bevacizumab (FIG. 3A) and rituximab (FIG. 3B) to NTP was measured using Bio Layer Interferometry Technology. Both antibodies were biotinylated using amine coupling and then bound individually to a BLITZ Streptavidin probe at 100 µg/mL. NTP at various concentrations was assayed for binding against the probe with association and dissociation periods of 120 seconds. Kinetic analysis was performed by BLITZ Evaluation software. Nano-picomolar affinities indicate strong binding between rituximab and NTP, and bevaciuzmab and NTP.

Example 4

Stability of Non-Toxic Nanoparticles (NTP) in PBS and Serum Compared to ABRAXANE® (ABX)

Antibody free NTP and ABRAXANE® (ABX) solutions were made to 30 µg/mL of Meerwein's Product of Paclitaxel and paclitaxel, respectively, in PBS. A baseline count of nanoparticles per mL was obtained using Malvern Nanosight technology. Then a range of dilutions was made for both solutions, and particle concentration was measured.

Figure 4A:
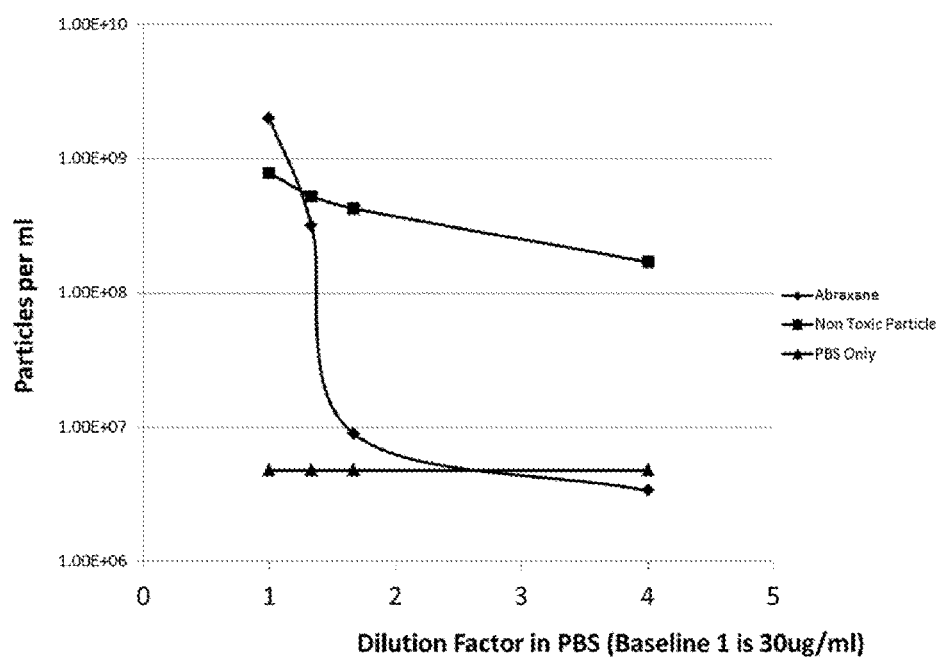
FIG. 4A shows the stability of nanoparticle complexes in PBS.

FIG. 4A shows the stability of ABX and NTP in saline. Abraxane nanoparticles began to fall apart around 1:1.33 dilution of initial solution until it reached the baseline PBS levels at ~1:2 dilution. NTP decreased linearly with dilution factor, suggesting no particle fall apart.

Figure 4B:
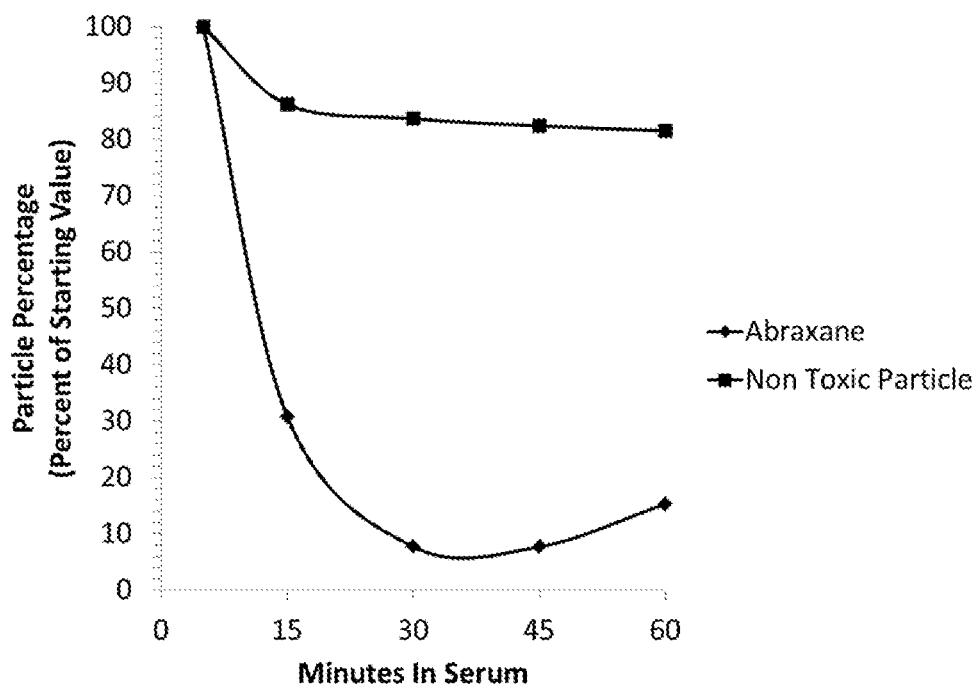
FIG. 4B shows the stability of nanoparticle complexes in serum.

FIG. 4B shows the stability of ABX and NTP in serum. NTP and ABX solutions were made to 250 µg/mL of Meerwein's Product of Paclitaxel and paclitaxel, respectively, in serum. Initial concentrations of nanoparticles were measured using Malvern Nanosight Technology, subsequent measurements are presented as a percentage of initial concentration. Concentrations of each solution were measured after 15, 30, 45, and 60 minutes in serum.

Example 5

Daudi Cell CD20 Blocking by NTP-Rituximab Complexes

Figure 5A:
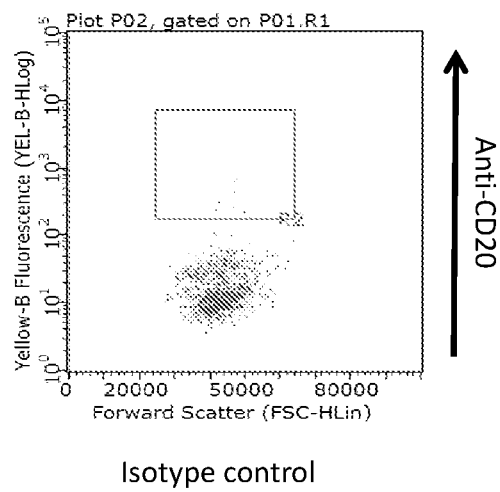
FIGS. 5A-5E show blocking of CD20-positive Daudi cells with isotype control (FIG. 5A), anti-CD20 antibody (FIG. 5B), ABRAXANE® (FIG. 5C), AR160 (FIG. 5D), NTP (FIG. 5E), rituximab-bound NTP (NTRit.
Figure 5B:
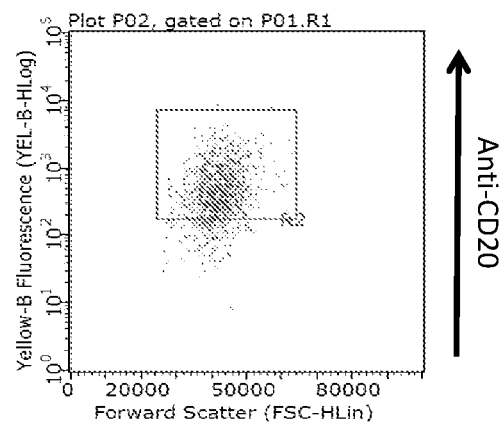

ABX, AR160, Non-toxic nanoparticle (NTP) and rituximab-bound NTP were prepared as described above or previously (see, e.g., PCT Pub. No. WO2014/055415, which is incorporated herein by reference in its entirety). The nanoparticles and unlabeled rituximab were co-incubated with CD20+ Daudi lymphoma cells for 30 minutes at room temperature. The cells were washed and subsequently stained with PE anti-human CD20. Isotype (FIG. 5A) and anti-CD20 (FIG. 5B) stained cells served as negative and positive controls, respectively.

Figure 5C:
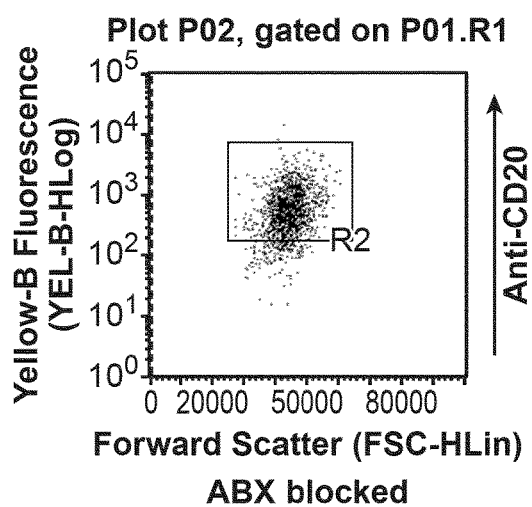
Figure 5D:
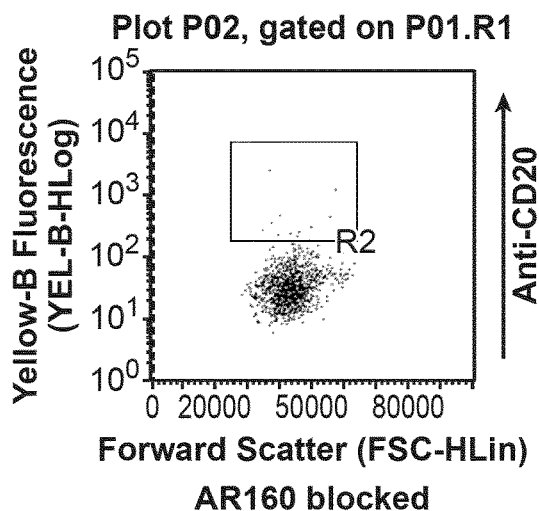
Figure 5E:
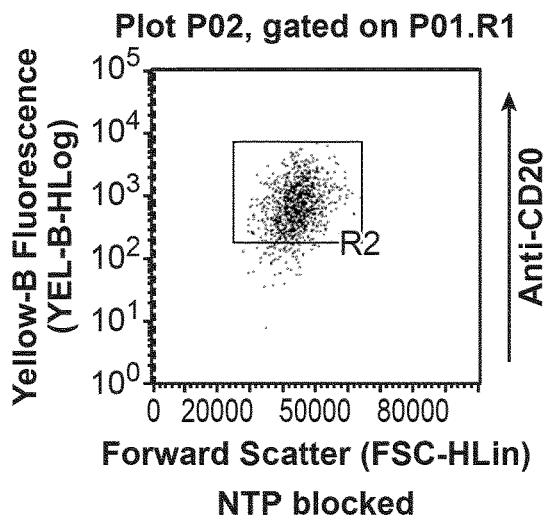
Figure 5F:
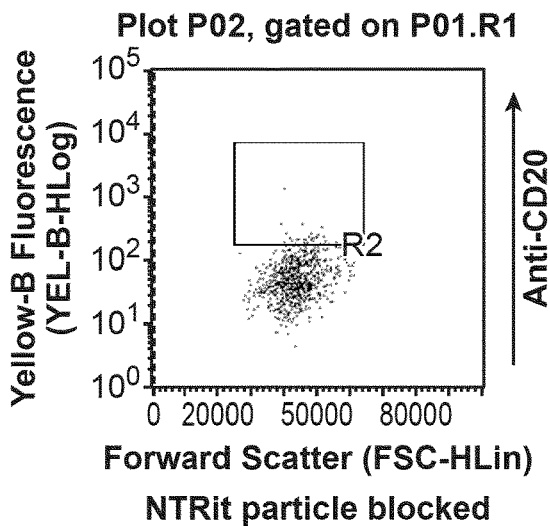
FIG. 5F), or rituximab alone (FIG. 5G).
Figure 5G:
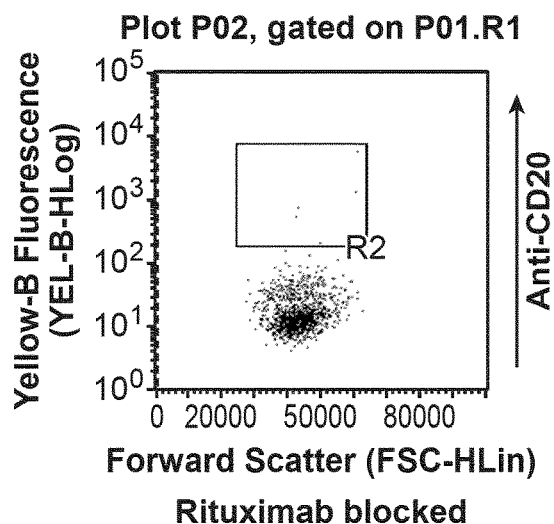

The results indicate the AR160 (FIG. 5D), rituximab loaded NT particles (NTRit; FIG. 5F), and rituximab (FIG. 5G) block subsequent binding of PE anti-human CD20, while ABX (FIG. 5C) and the NT nanoparticle (FIG. 5E) alone do not. This shows that the the rituximab in the context of AR160 and rituximab-loaded NT particles retains its ligand binding properties.

Example 6

Albumin-Paclitaxel Nanoparticles with Reduced Paclitaxel

Albumin-paclitaxel nanoparticles having reduced amounts of paclitaxel compared to ABRAXANE® are formed.

For example, less than 30 mg (e.g., 1 mg to 25 mg) paclitaxel is dissolved in a solvent (e.g., methylene chloride; or chloroform and ethanol). The solution is added to 27.0 mL of human serum abumin solution (1% w/v). The mixture is homogenized for 5 minutes at low RPM in order to form a crude emulsion, and then transferred into a high pressure homogenizer. The emulsification is performed at 9000-40,000 psi while recycling the emulsion for at least 5 cycles. The resulting system is transferred into a rotary evaporator, and methylene chloride is rapidly removed at 40° C., at reduced pressure (30 mm Hg), for 20-30 minutes. Optionally, the dispersion is filtered through a 0.22 micron filter.

The filtered nanoparticles may be lyophilized and stored.

Example 7

Albumin-Paclitaxel-Therapeutic Agent Nanoparticles with Reduced Paclitaxel

Albumin-paclitaxel-therapeutic agent nanoparticles having reduced amounts of paclitaxel compared to ABRAXANE® are formed.

For example, albumin-paclitaxel nanoparticles are formed as described in Example 6. A therapeutic agent (e.g., cisplatin) is incubated with the nanoparticles at a ratio of about 10:1 (nanoparticles:agent) at room temperature for 30 min. Free therapeutic agent (e.g., cisplatin) is measured by HPLC in the supernatant after nanoparticle particulate is removed.

Example 8

Albumin-Paclitaxel-Antibody Nanoparticles with Reduced Paclitaxel

Albumin-paclitaxel-antibody nanoparticles having reduced amounts of paclitaxel compared to ABRAXANE® are formed.

For example, albumin-paclitaxel nanoparticles are formed as described in Example 6. Nanoparticles (10 mg) are combined with an antibody (e.g., bevacizumab) (4 mg), and 840 µl of 0.9% saline is added to give a final concentration of 10 mg/ml and 2 mg/ml of nanoparticles and antibody, respectively. The mixture is incubated for 30 minutes at room temperature to allow particle formation.

An antibody-albumin-paclitaxel-therapeutic agent nanoparticle complex may be formed. Optionally, antibody is incubated with albumin-paclitaxel-therapeutic agent nanoparticles (from Example 7) to form antibody-albumin-paclitaxel-therapeutic agent nanoparticle complexes. Alternatively, the antibody-albumin-paclitaxel nanoparticles my be incubated with the therapeutic agent to form antibody-albumin-paclitaxel-therapeutic agent nanoparticle complexes.

What is claimed is:

1. A nanoparticle complex comprising albumin, 20-acetoxy-4-deacetyl-5-epi-20,O-secotaxol, and antibodies having an antigen-binding domain, wherein the antibodies are bound to the albumin through non-covalent bonds and are arranged on an outside surface of the nanoparticle complexes and wherein the 20-acetoxy-4-deacetyl-5-epi-20,O-secotaxol is less toxic than paclitaxel.

2. The nanoparticle complex of claim 1, further comprising a therapeutic agent.

3. The nanoparticle complex of claim 2, wherein the therapeutic agent is selected from abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, hydroxyurea, imatinib, lapatinib, leuprorelin, melphalan, methotrexate, mitoxantrone, nedaplatin, nilotinib, paclitaxel, pazopanib, pemetrexed, picoplatin, romidepsin, satraplatin, sorafenib, vemurafenib, sunitinib, teniposide, triplatin, vinblastine, vinorelbine, vincristine, or cyclophosphamide.

4. The nanoparticle complex of claim 1, wherein the albumin and the paclitaxel derivative have a relative weight ratio of less than about 10:1.

5. The nanoparticle complex of claim 1, wherein the antigen is CD3, CD 19, CD20, CD38, CD30, CD33, CD52, PD-1, PD-L1, PD-L2, CTLA-4, RANK-L, GD-2, Ly6E, HER3, EGFR, DAF, ERBB-3 receptor, CSF-IR, HER2, STEAP1, CD3, CEA, CD40, OX40, Ang2-VEGF, or VEGF.

6. The nanoparticle complex of claim 1 which is lyophilized.

7. The nanoparticle complex of claim 6 which is stable at about 20° C. to about 25° C. for up to about 12 months or longer.

8. The nanoparticle complex of claim 1, which is not oligomerized.

9. The nanoparticle complex of claim 1 having a size between about 70 nm and about 800 nm.

10. The nanoparticle complex of claim 1 having a size between about 100 nm and about 200 nm.

11. The nanoparticle complex of claim 1, wherein the antibodies are selected from alemtuzumab, atezolizumab, bevacizumab, cetuximab, denosumab, dinutuximab, ipilimumab, nivolumab, obinutuzumab, ofatumumab, panitumumab, pembrolizumab, pertuzumab, rituximab, avelumab, durvalumab, pidilizumab, BMS 936559, OKT3, and trastuzumab.

12. The nanoparticle complex of claim 1, wherein the albumin is human serum albumin.

13. The nanoparticle complex of claim 12, wherein the albumin is recombinant human serum albumin.

14. The nanoparticle complex of claim 1 having a dissociation constant between about $1 \times 10^{-11}$ M and about $1 \times 10^{-9}$ M.

15. A composition comprising the nanoparticle of claim 1.

16. A method for killing cancer cells in a population of cancer cells, the method comprising contacting the cells with an effective amount of the nanoparticle of claim 1, wherein said nanoparticle is maintained in contact with said cells for a sufficient period of time to kill cancer cells.

17. A method for treating cancer in patient in need thereof, the method comprising administering to the patient the composition of claim 15.

* * * * *